US012415926B2

(12) United States Patent
Vendrell et al.

(10) Patent No.: US 12,415,926 B2
(45) Date of Patent: Sep. 16, 2025

(54) SMALL TUNABLE FLUOROPHORES FOR THE DETECTION AND IMAGING OF BIOMOLECULES

(71) Applicant: The University Court of the University of Edinburgh, Edinburgh (GB)

(72) Inventors: Marc Vendrell, Edinburgh (GB); Antonio Fernandez, Edinburgh (GB); Sam Benson, Edinburgh (GB); Nicole D. Barth, Edinburgh (GB); Fabio De Moliner, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 996 days.

(21) Appl. No.: 17/439,077

(22) PCT Filed: Mar. 17, 2020

(86) PCT No.: PCT/EP2020/057308
§ 371 (c)(1),
(2) Date: Sep. 14, 2021

(87) PCT Pub. No.: WO2020/187919
PCT Pub. Date: Sep. 24, 2020

(65) Prior Publication Data
US 2022/0154003 A1    May 19, 2022

(30) Foreign Application Priority Data

Mar. 18, 2019  (GB) .................................... 1903664

(51) Int. Cl.
| *C09B 51/00* | (2006.01) |
| *A61B 3/12* | (2006.01) |
| *A61B 5/00* | (2006.01) |
| *A61K 49/00* | (2006.01) |
| *C07D 235/08* | (2006.01) |
| *C07D 249/18* | (2006.01) |
| *C07D 285/14* | (2006.01) |
| *C07D 293/12* | (2006.01) |
| *G01N 21/64* | (2006.01) |

(52) U.S. Cl.
CPC ............ *C09B 51/00* (2013.01); *A61B 3/1241* (2013.01); *A61B 5/0066* (2013.01); *A61B 5/0071* (2013.01); *A61B 5/0095* (2013.01); *A61K 49/0021* (2013.01); *C07D 235/08* (2013.01); *C07D 249/18* (2013.01); *C07D 285/14* (2013.01); *C07D 293/12* (2013.01); *G01N 21/6428* (2013.01); *G01N 2021/6439* (2013.01)

(58) Field of Classification Search
CPC .. C09B 51/00; A61K 49/0021; C07D 235/08; C07D 249/18; C07D 285/14; C07D 293/12; A61B 3/1241; A61B 5/0066; A61B 5/0095; G01N 21/6428; G01N 2021/6439
See application file for complete search history.

(56) References Cited

U.S. PATENT DOCUMENTS 7,960,439 B1    6/2011 Zhao
2016/0229887 A1*  8/2016 Martinez Botella ... A61K 31/58

FOREIGN PATENT DOCUMENTS

JP    2011-184374 A    9/2011

OTHER PUBLICATIONS

Ku et al., 33(3) Bull. Korean Chem. Soc. 1029-1036 (2012) (CAS Abstract) (Year: 2012).*
Ciofini et al., 116(22) J. Phy. Chem. C. 11946-11955 (2012) (CAS Abstract) (Year: 2012).*
Bella, M., et al., "Synthesis of 9-ethyl[1,2,5]selenadiazolo[3,4,h]quinolones by the application of modified Gould-Jacobs reaction to the N-ethyl1-2,1,3-benzoselenadiazol-4-amine," Arkivoc, 2014(5):181-198 (2014) (18 pages).

(Continued)

*Primary Examiner* — Timothy R Rozof
(74) *Attorney, Agent, or Firm* — Foley & Lardner LLP

(57)    ABSTRACT

The invention relates to small, conjugatable, orthogonal and tunable fluorophores for imaging of small bioactive molecules. The invention further relates to processes for the preparation of the compounds, and uses of the compounds in therapeutic, diagnostic, surgery and analytical applications. The invention provides a compound of formula (I), a derivative or a salt thereof. Wherein X is selected from the group consisting of NH, O, S, SeR5R6, CR7R8; R1 is selected from the group consisting of amines, alcohols, thiols, thiophenols, selenols, selenophenols and aryl groups; R2 and R3 are independently H or a halogen; R4 tis either H, nitro or cyano; R5 is either absent or methyl or oxygen; R6 is either absent or methyl or oxygen; and R7 and R8 are independently selected from the group consisting of linear or cyclic alkyl groups containing halogen, amino, cyano or carboxylic ester substituents, and alkyl aryl groups.

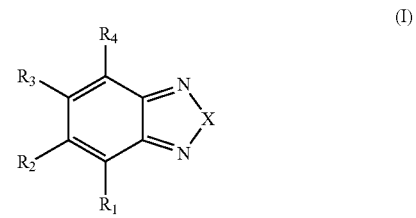

(I)

13 Claims, 7 Drawing Sheets

(56) References Cited

OTHER PUBLICATIONS

Figure 1:
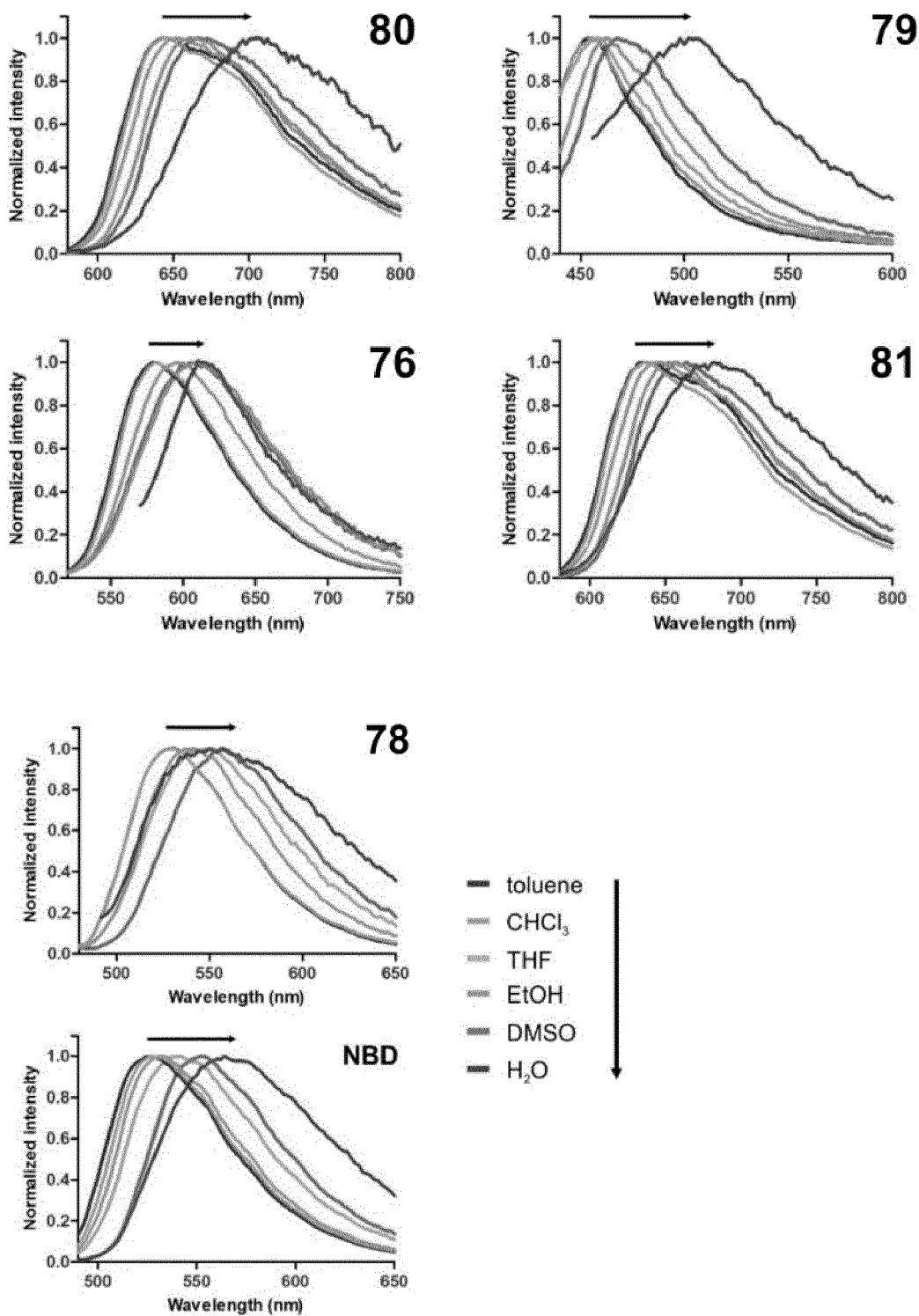

Idris, I., et al., "Effective modulation of the photoluminescence properties of 2,1,3-benzothiadiazoles and 2,1,3-benzoselenadiazoles by Pd-catalyzed C—H bond arylations," J. Mat. Chem., 6(7):1731-1737 (2018) (7 pages).

Lesko, J., et al., "Mass Spectra of Some 4- and 5-Substitued Derivatives of Benzoselenadiazoles," Molecules, 5(12):937-940 (2000) (4 pages).

Search Report on GB Application No. GB1903664.9, dated Aug. 21, 2019 (5 pages).

Shome, S., et al., "Access to small molecule semiconductors via C—H activation for photovoltaic applications", Chemical Communications, pp. 7322-7325.

Wang, Y., et al., "Thermally activated delayed fluorescence sensitzer for D-A-A type emitters with orange-red light emission", Journal of Materials Chemistry C, pp. 10030-10035.

Benson, S., et al., "SCOTfluors: Small, Conjugatable, Orthogonal, and Tunable Fluorophores for In Vivo Imaging of Cell Metabolism," Angewandte Chemie, Int. Ed., 58(21):6911-6915 (2019) (5 pages).

International Search Report and Written Opinion on PCT/EP2020/057308 dated Aug. 24, 2020 (21 pages).

Jenkinson, D.R., et al., "The Synthesis and Photophysical Analysis of a Series of 4-Nitrobenzochalcogenadiazoles for Super-Resolution Microscopy," Chem.—A European Journal, 23(51):12585-12592 (2017) (11 pages).

Yee Tan, H., et al., "Direct One-Step Fluorescent Labeling of O-GlcNAc-Modified Proteins in Live Cells Using Metabolic Intermediates," J. Am. Chem. Soc., 140(45):15300-15308 (2018) (9 pages).

Zhang, H., et al., "An endoplasmic reticulum-targetable fluorescent probe for highly selective detection of hydrogen sulfide," Org. & Biomol. Chem., 17(6):1436-1441 (2019) (6 pages).

\* cited by examiner

SCOTfluor-84

SCOTfluor-90

SMALL TUNABLE FLUOROPHORES FOR THE DETECTION AND IMAGING OF BIOMOLECULES

CROSS-REFERENCE TO RELATED PATENT APPLICATIONS

This application is a U.S. National Phase Application under 35 U.S.C. § 371 of International Application No. PCT/EP2020/057308, filed Mar. 17, 2020, which claims the benefit of and priority to GB Appl. No. 1903664.9, filed Mar. 18, 2019, each of which are incorporated herein by reference in their entirety.

FIELD OF THE INVENTION

The invention relates to small, conjugatable, orthogonal and tunable fluorophores for imaging of small bioactive molecules. The invention further relates to processes for the preparation of the compounds, and uses of the compounds in therapeutic, diagnostic, surgery and analytical applications.

BACKGROUND OF THE INVENTION

Metabolites are essential biochemical components, with their transport and localization regulating most biological functions. Despite advances in fluorescence imaging to label small biomolecules, there are few approaches to image in situ small metabolites in live cells and intact organisms.

Most metabolites do not contain groups that allow direct visualization and need to be modified with exogenous chromophores. Most in vivo imaging fluorophores rely on near-infrared (NIR) chemical scaffolds as they allow deep penetration with minimal photodamage and low tissue autofluorescence. However, fluorescent labels, in particular red and near-infrared (NIR) fluorophores, are bulky structures that can impair how small biomolecules traffic within cells.

Nitrobenzodioxazole (NBD) has been widely used because of its small size and neutral character. These properties have facilitated labelling biomolecules with retention of their native properties. However, NBD (emission~540 nm) is incompatible with other green fluorescent reporters (e.g. GFP) and has limited application for in vivo use.

Therefore, there remains the need for fluorogenic amino acids to label peptides, sugar or other bioactive molecules without affecting their properties which allow direct imaging of essential metabolites in live cells and in vivo using small-sized multi-color fluorophores.

STATEMENT OF THE INVENTION

The present invention provides a collection of Small, Conjugatable, Orthogonal and Tunable Fluorophores—named SCOTfluors—with tunable emission covering the entire visible spectrum. SCOTfluors include the smallest fluorophores emitting in the NIR window (650-900 nm) reported to date.

The fluorophores of the invention can be used to label cancer cells, immune cells as well as stem cells for regenerative cell-based therapies or fluorescence-guided surgery.

The compounds of the invention are also suitable for other optical imaging modalities beyond fluorescence. For example, they can be used as multimodal reagents as they can be readily detected under Surface-Enhanced Raman Scattering upon conjugation to metal surfaces, for optoacoustic imaging as they absorb NIR light and also for optical coherence tomography.

In particular, it is hereby provided a compound of formula (I), a derivative or a salt thereof

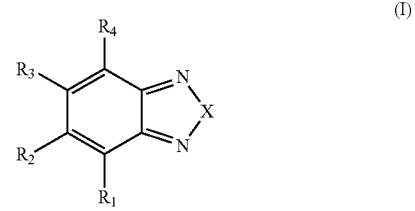

(I)

wherein
X is selected from the group consisting of NH, O, S, SeR5R6, and CR7R8;
R1 is selected from the group consisting of amines, alcohols, thiols, thiophenols, selenols, selenophenols and aryl groups;
R2 and R3 are independently H or a halogen;
R4 is either H, nitro or cyano;
R5 and R6 are independently either absent or methyl or oxygen; and
R7 and R8 are independently selected from the group consisting of linear or cyclic alkyl groups containing halogen, amino, cyano or carboxylic ester substituents, and alkyl aryl groups.

Preferably, X is CR7R8 or SeR5R6.
Preferably, R1 is selected from the group consisting of amines, anilines, thiols and thiophenols, even more preferably R1 is an amine, preferably propylamine, diethylamine, isoserine, glucosamine, aminohexanoic acid.
Preferably, R2 and R3 are H.
Preferably, R4 is nitro.
Preferably, R5 is absent.
Preferably, R6 is absent.
Preferably, R7 and R8 are independently selected from linear alkyl, cyclic alkyl or aryl groups, more preferably R7 and R8 are independently methyl or cyclohexyl groups.

The compound is preferably selected from the group consisting of SCOTfluor 27-121, SCOTfluor 124-160 reported below, and a derivative or a salt thereof.

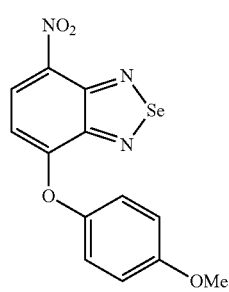

SCOTfluor-27

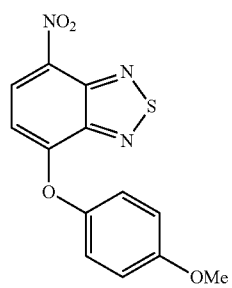

SCOTfluor-28

-continued
SCOTfluor-29
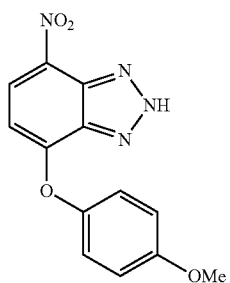
SCOTfluor-30
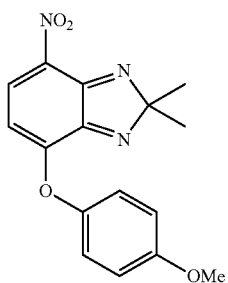
SCOTfluor-31
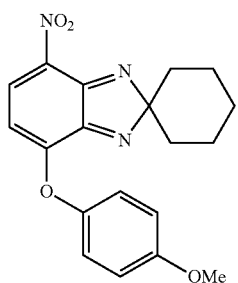
SCOTfluor-32
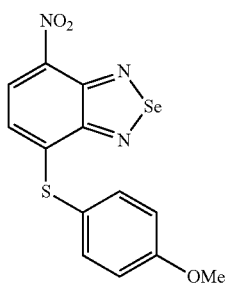
SCOTfluor-33
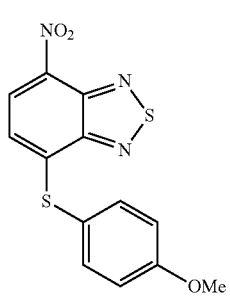
SCOTfluor-34
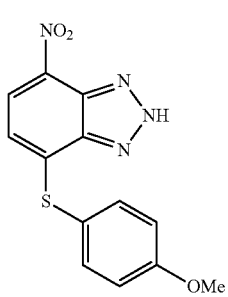
SCOTfluor-35
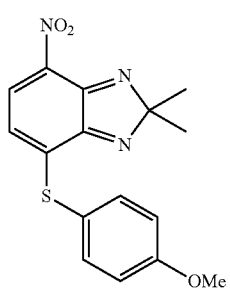
SCOTfluor-36
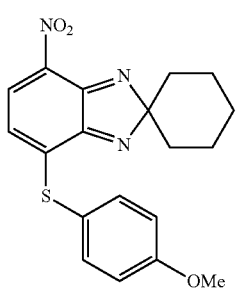
SCOTfluor-37
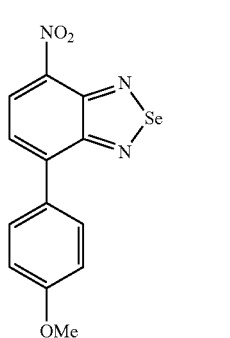
SCOTfluor-38
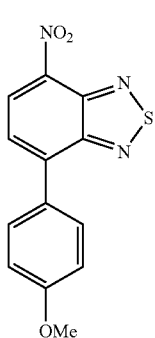

-continued
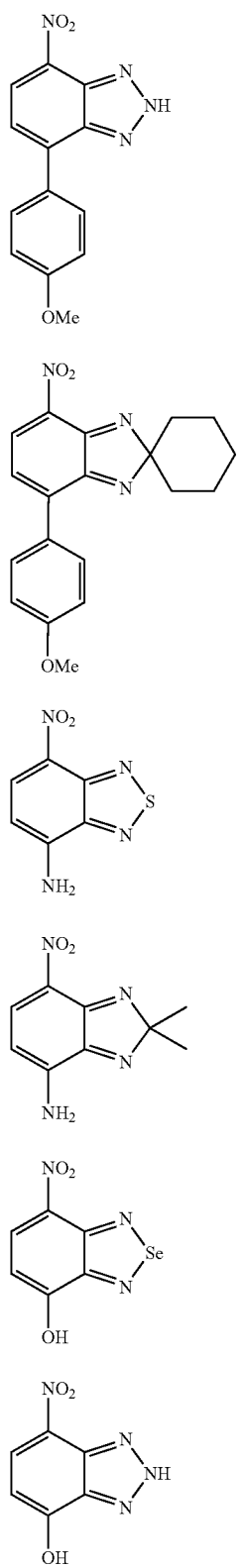
SCOUTfluor-39
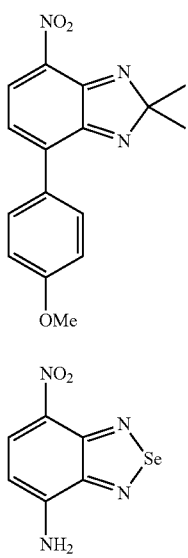
SCOUTfluor-40
SCOUTfluor-41
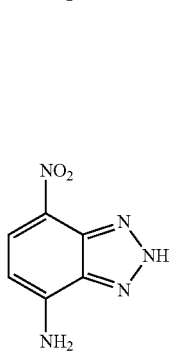
SCOUTfluor-42
SCOUTfluor-43
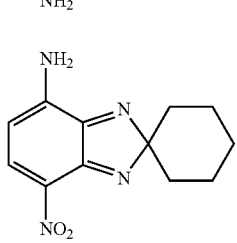
SCOUTfluor-44
SCOUTfluor-45
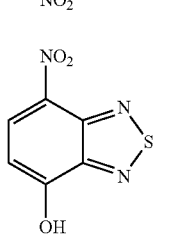
SCOUTfluor-46
SCOUTfluor-47
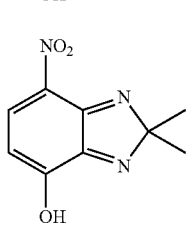
SCOUTfluor-48
SCOUTfluor-49
SCOUTfluor-50

-continued
SCOUTfluor-51
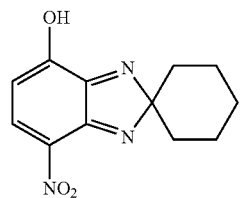
SCOUTfluor-52
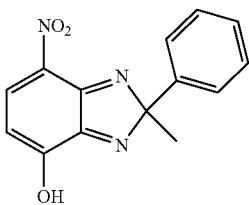
SCOTfluor-53
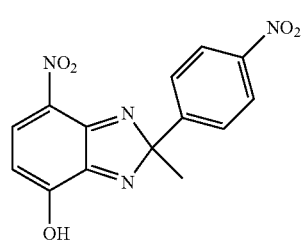
SCOTfluor-54
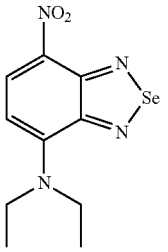
SCOTfluor-55
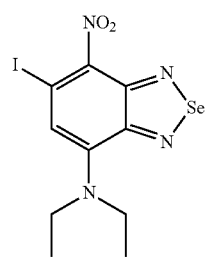
SCOTfluor-56
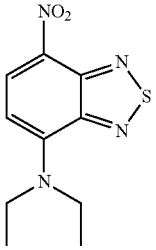
SCOTfluor-57
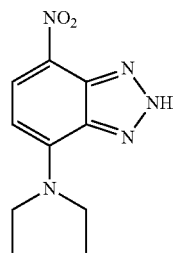
SCOTfluor-58
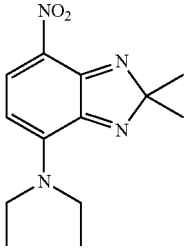
SCOTfluor-59
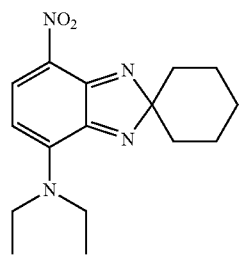
SCOTfluor-60
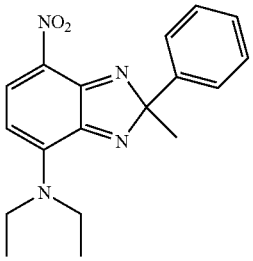
SCOTfluor-61
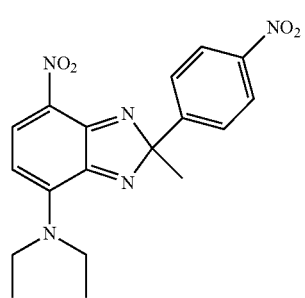
SCOTfluor-62
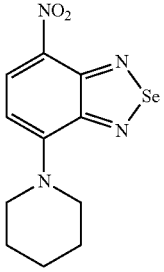

-continued
SCOTfluor-63
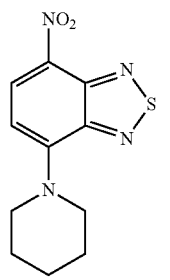
SCOTfluor-64
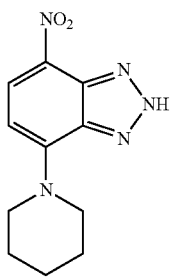
SCOTfluor-65
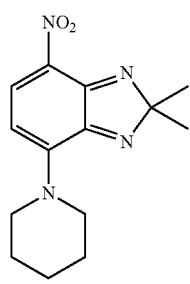
SCOTfluor-66
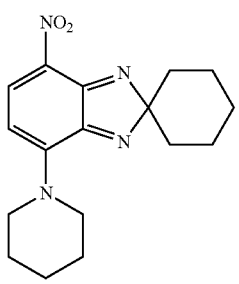
SCOTfluor-67
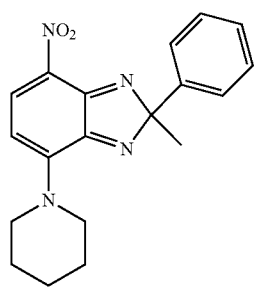
SCOTfluor-68
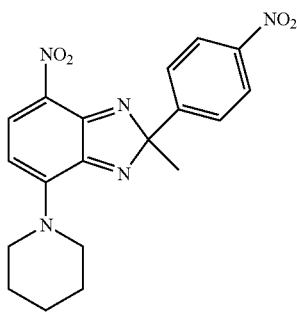
SCOTfluor-69
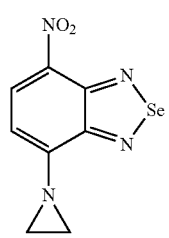
SCOTfluor-70
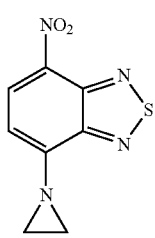
SCOTfluor-71
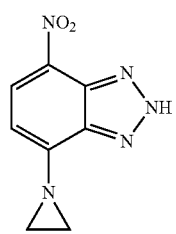
SCOTfluor-72
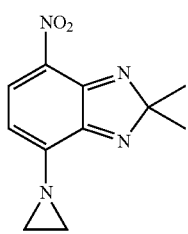
SCOTfluor-73
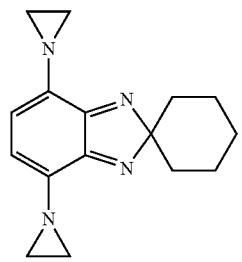
SCOTfluor-74
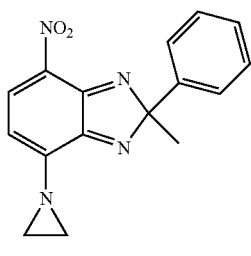

-continued
SCOTfluor-75
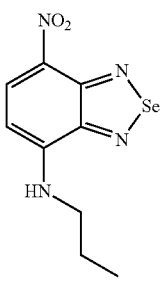
SCOTfluor-76
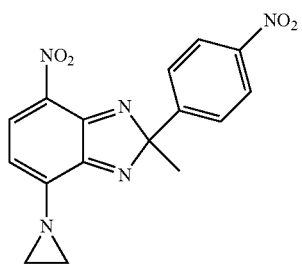
SCOTfluor-77
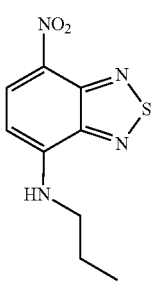
SCOTfluor-78
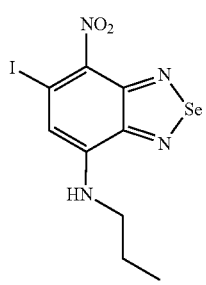
SCOTfluor-79
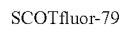
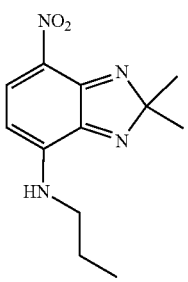
SCOTfluor-80
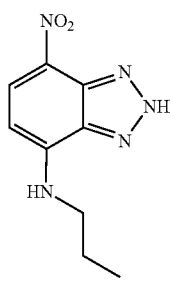
SCOTfluor-81
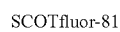
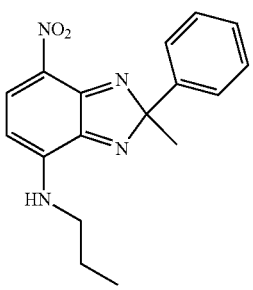
SCOTfluor-82
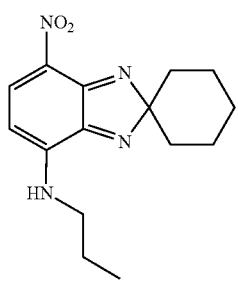
SCOTfluor-83
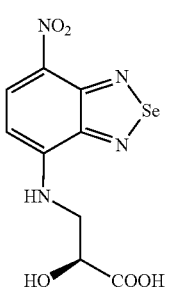
SCOTfluor-84
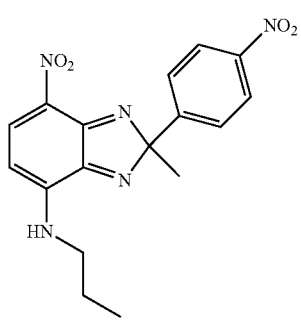

-continued
SCOTfluor-85
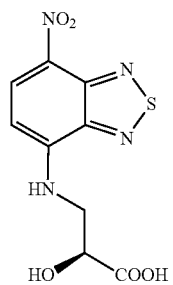
SCOTfluor-86
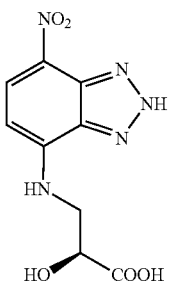
SCOTfluor-87
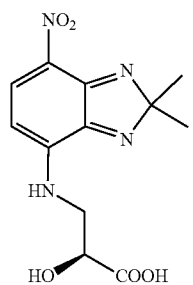
SCOTfluor-88
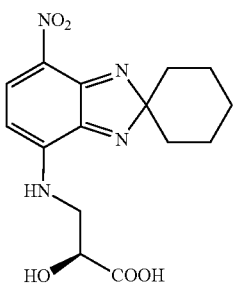
SCOTfluor-89
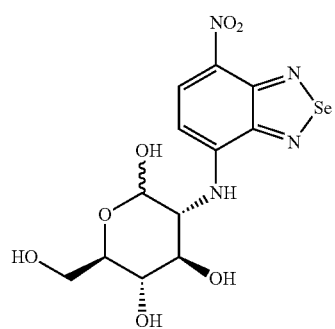
SCOTfluor-90
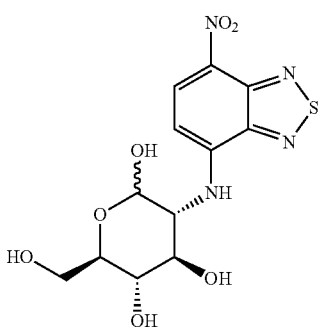
SCOTfluor-91
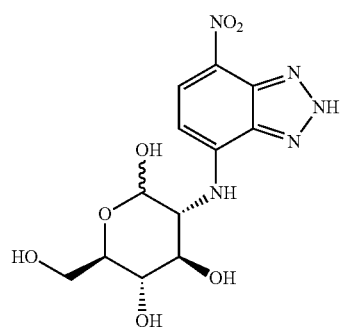
SCOTfluor-92
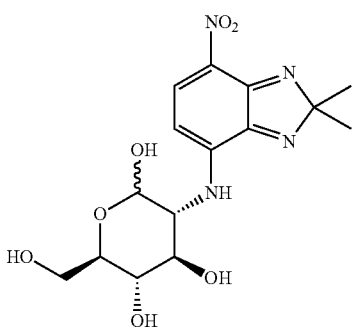
SCOTfluor-93
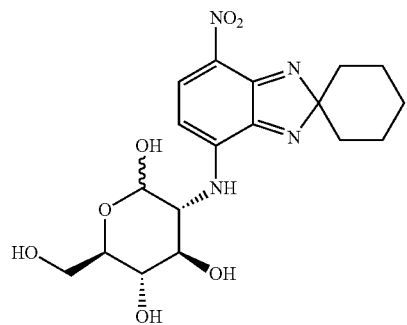
SCOTfluor-94
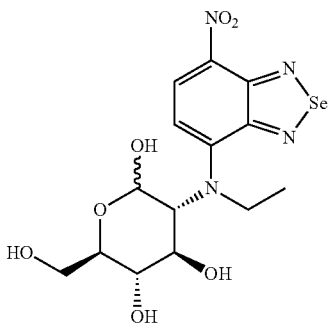

-continued
SCOTfluor-95
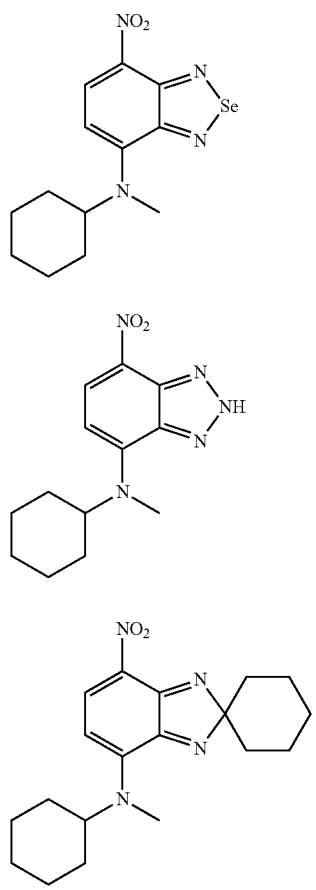
SCOTfluor-96
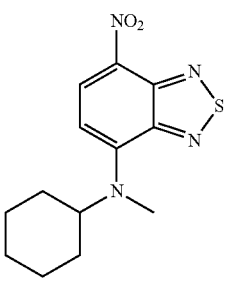
SCOTfluor-97
SCOTfluor-98
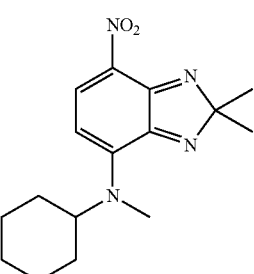
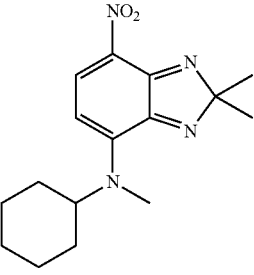
SCOTfluor-99
SCOTfluor-100
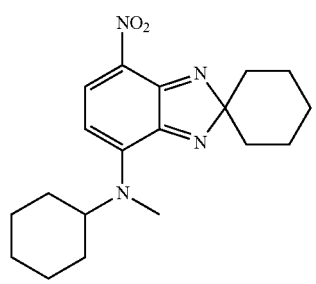
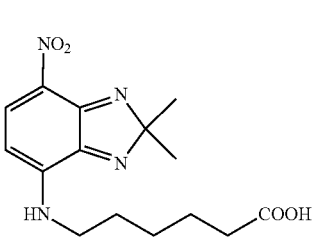
SCOTfluor-101
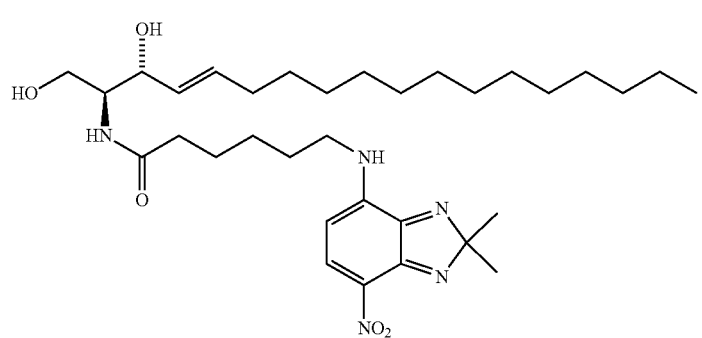
SCOTfluor-102
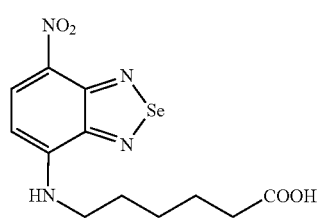

SCOTfluor-103
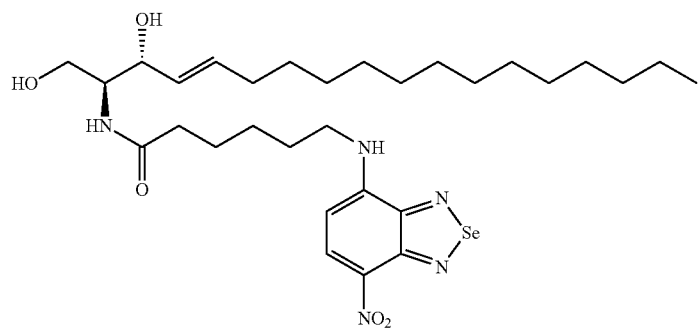
SCOTfluor-104
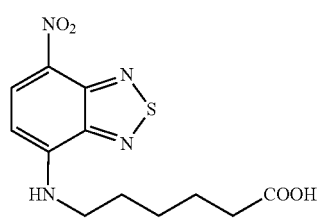
SCOTfluor-105
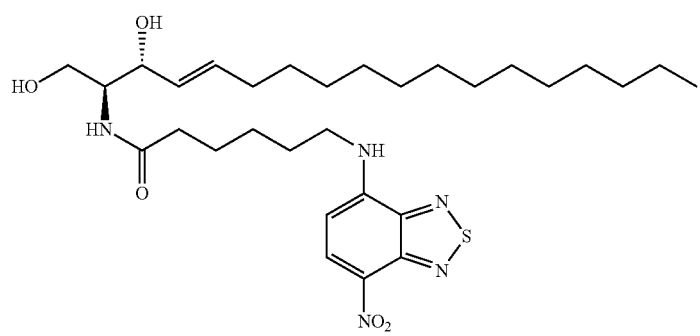
SCOTfluor-106
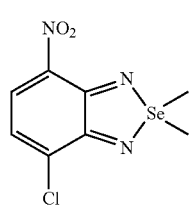
SCOTfluor-107
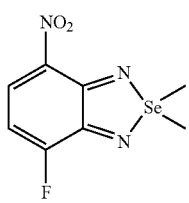
SCOTfluor-108
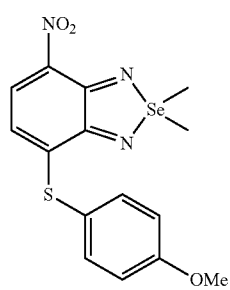
SCOTfluor-109
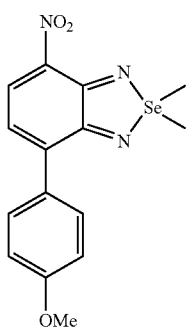

-continued
SCOTfluor-110
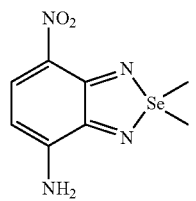
SCOTfluor-111
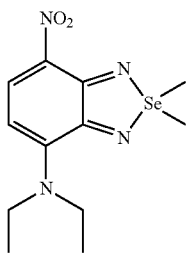
SCOTfluor-112
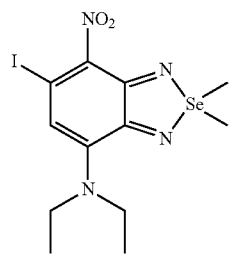
SCOTfluor-113
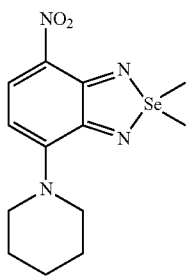
SCOTfluor-114
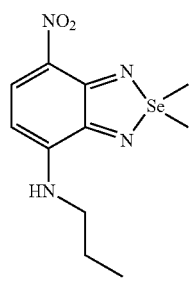
SCOTfluor-115
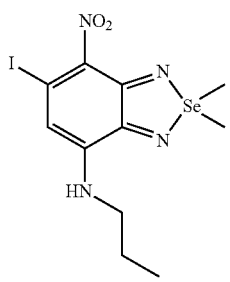
SCOTfluor-116
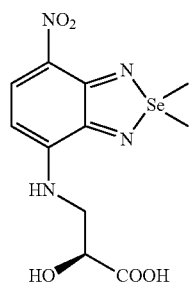
SCOTfluor-117
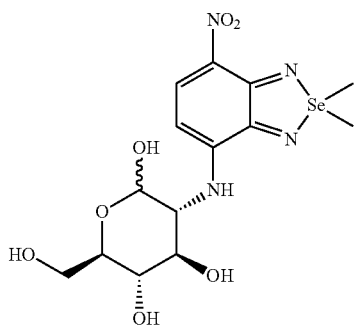
SCOTfluor-118
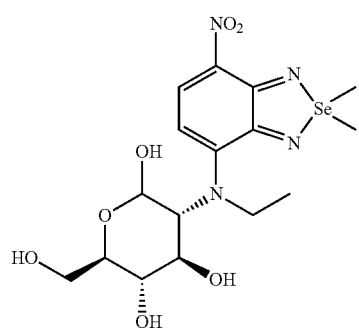
SCOTfluor-119
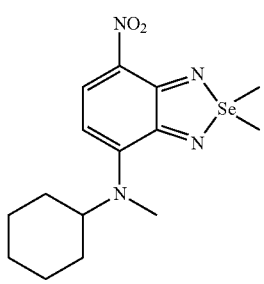

-continued
SCOTfluor-120
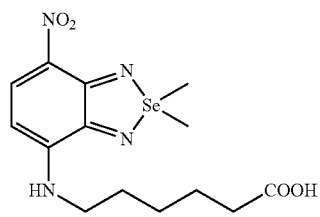
SCOTfluor-121
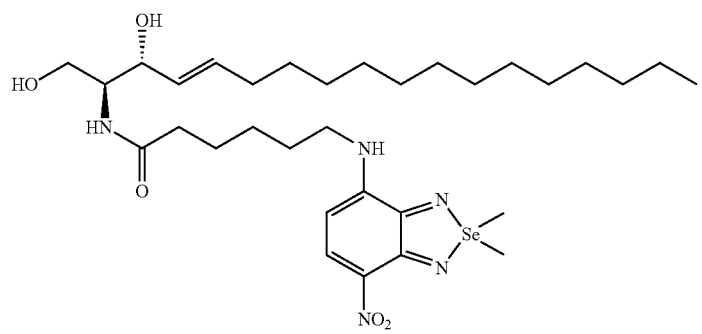
SCOTfluor-124
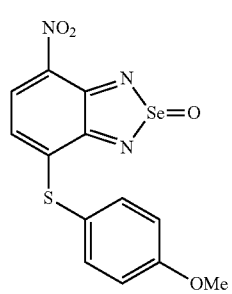
SCOTfluor-125
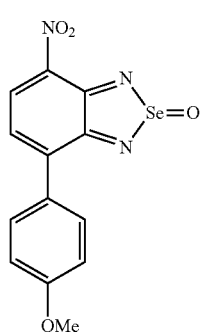
SCOTfluor-126
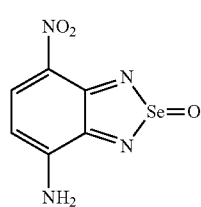
SCOTfluor-127
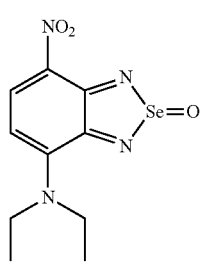
SCOTfluor-128
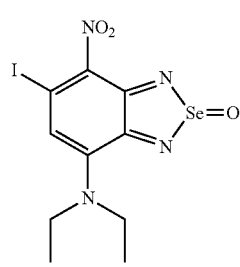
SCOTfluor-129
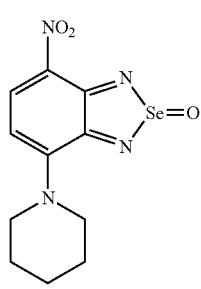

SCOTfluor-130
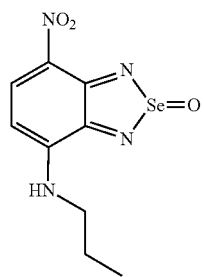
SCOTfluor-131
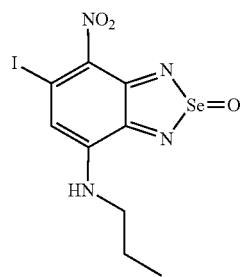
SCOTfluor-132
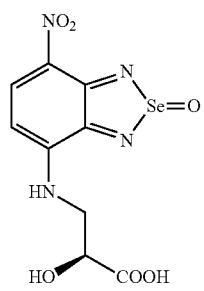
SCOTfluor-133
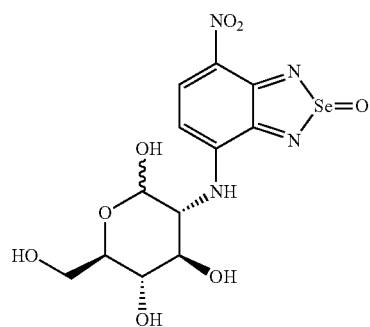
SCOTfluor-134
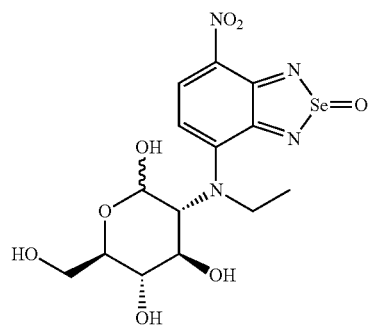
SCOTfluor-135
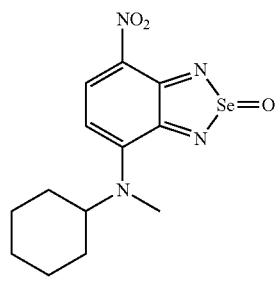
SCOTfluor-136
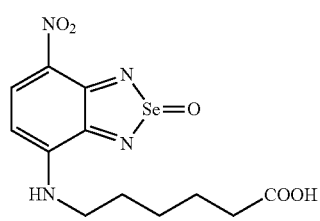
SCOTfluor-137
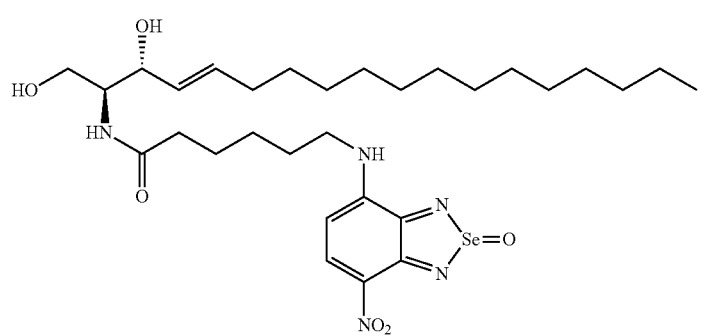

SCOTfluor-138
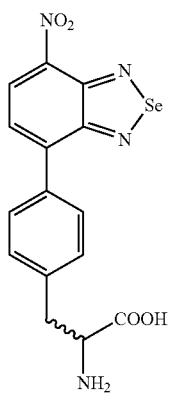
SCOTfluor-139
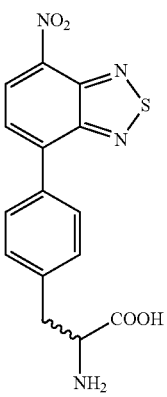
SCOTfluor-140
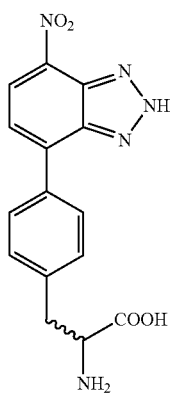
SCOTfluor-141
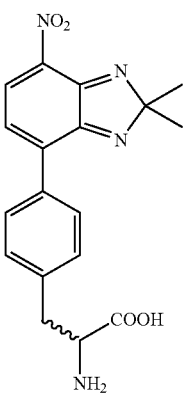
SCOTfluor-142
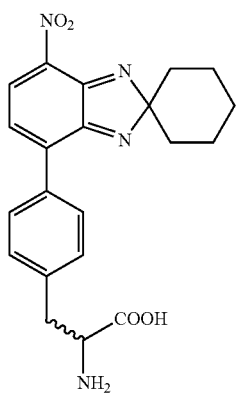
SCOTfluor-143
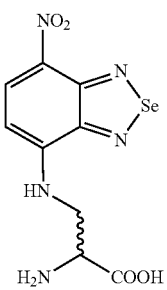
SCOTfluor-144
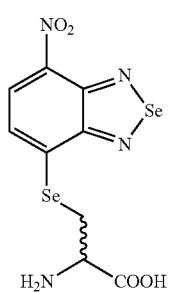
SCOTfluor-145
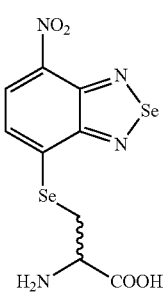

-continued
SCOTfluor-146
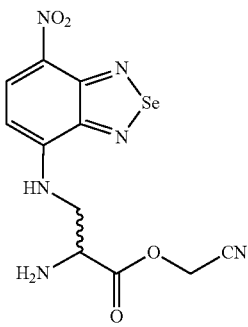
SCOTfluor-147
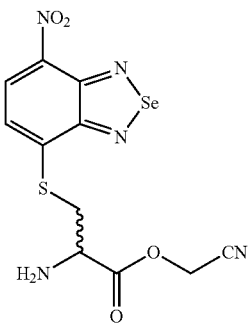
SCOTfluor-148
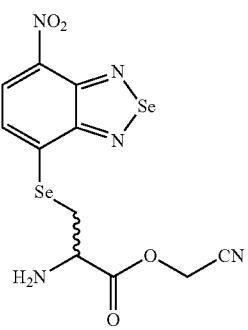
SCOTfluor-149
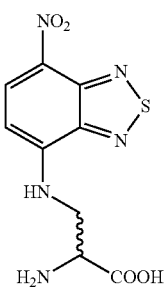
SCOTfluor-150
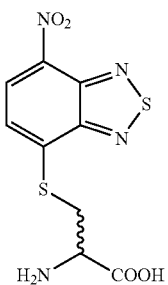
SCOTfluor-151
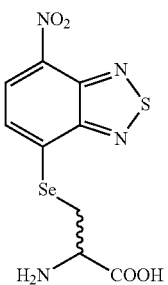
SCOTfluor-152
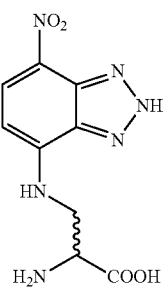
SCOTfluor-153
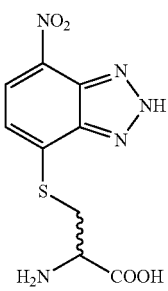
SCOTfluor-154
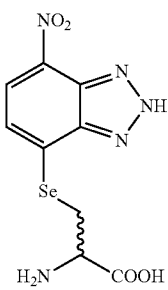
SCOTfluor-155
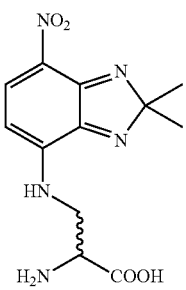

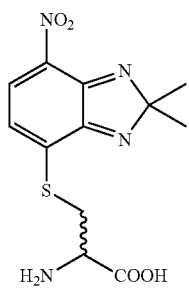
SCOTfluor-156

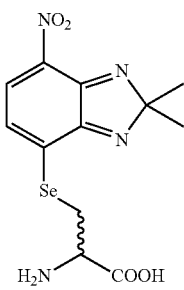
SCOTfluor-157

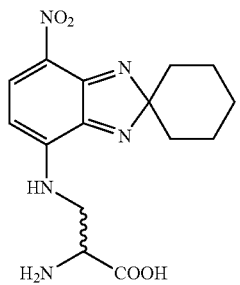
SCOTfluor-158

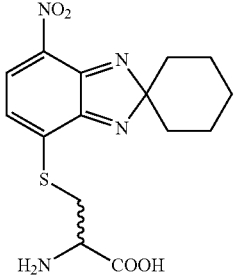
SCOTfluor-159

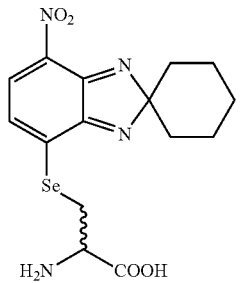
SCOTfluor-160

More preferably the compound is selected from the group consisting of a derivative and a salt of the SCOTfluor 27-121 or SCOTfluor 124-160 as defined above.

Even more preferably, the compound is selected from the group consisting of SCOTfluor-76, 78, 79, 80, 81, 84, 89, 90, 101 as defined above, and a derivative or a salt thereof.

Generally, the compounds of the invention may be prepared by a process comprising the step of:
a) providing an intermediate of formula II

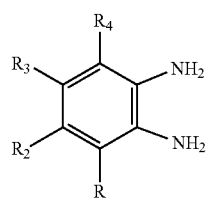
(II)

wherein
R is a halogen atom, preferably is Br, Cl or F;
$R_2$ and $R_3$ are independently H or a halogen, preferably H;
$R_4$ is either H, nitro or cyano, preferably nitro;
b) linking the two amino groups; and
c) performing a substitution reaction to replace the halogen with a nucleophile group. Preferably the nucleophile group is an amine, aniline, a thiol or thiophenol.

In particular, the preparation of SCOTfluors may be achieved in two synthetic steps from a common intermediate of formula II. First, the two amino groups in the intermediate of formula II are linked with different bridging groups. All the reactions proceed similarly for fluoride and chloride derivatives. Triazole derivatives can be synthesized by reaction with sodium nitrite in acidic media at room temperature, thioderivatives can be obtained by condensation with N-thionylaniline under heating, and selenium analogues can be prepared by reaction with $SeO_2$ under reflux in EtOH. Finally, carbon derivatives can be synthesized by Cu-catalyzed coupling using ketones, respectively. Secondly, halogenated compounds are derivatized with nucleophiles under mild conditions.

The present invention also provides compounds, which are precursors of the compounds of Formula (I). The precursor compound is of Formula (Ia) or a derivative or salt thereof

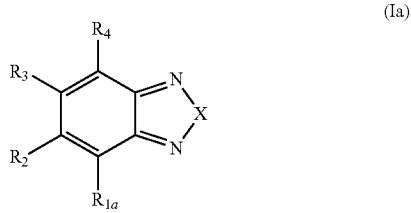
(Ia)

Formula (Ia) is identical to Formula (I) except for $R_{1a}$, which is halogen, preferably Cl or F. In particular, X, $R_2$, $R_3$, $R_4$ are as defined as above and $R_{1a}$ is halogen.

The precursor compound is preferably selected from the group consisting of SCOTfluor 1-26, SCOTfluor 122-123, SCOTfluor 161-162 defined below, and a derivative or a salt thereof.

SCOTfluor-1

SCOTfluor-2

SCOTfluor-3
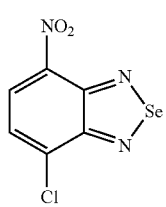

SCOTfluor-4
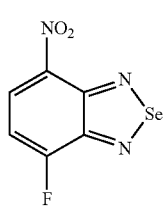

SCOTfluor-5
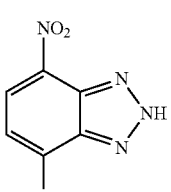

SCOTfluor-6
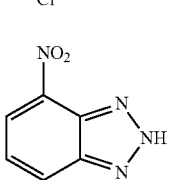

SCOTfluor-7
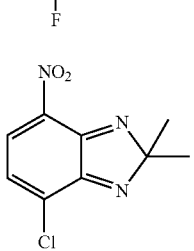

SCOTfluor-8
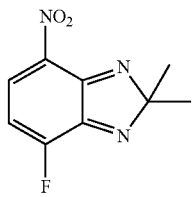

SCOTfluor-9
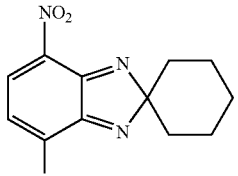

SCOTfluor-10
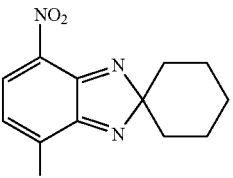

SCOTfluor-11
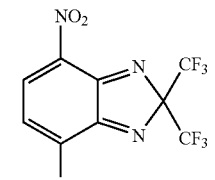

SCOTfluor-12
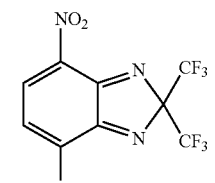

SCOTfluor-13
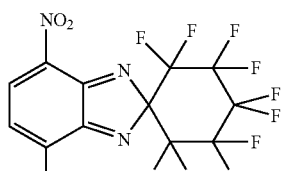

SCOTfluor-14
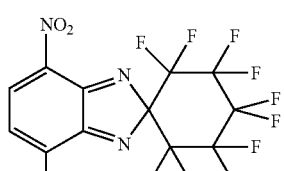

SCOTfluor-15
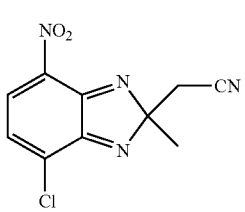

-continued

SCOTfluor-16

SCOTfluor-17

SCOTfluor-18

SCOTfluor-19

SCOTfluor-20

SCOTfluor-21

SCOTfluor-22

-continued

SCOTfluor-23

SCOTfluor-24

SCOTfluor-25

SCOTfluor-26

SCOTfluor-122

SCOTfluor-123

SCOTfluor-161

SCOTfluor-162

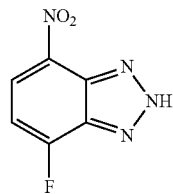

The present invention also provides a dye-labelled agent, a dye-labelled cell or a dye-labelled molecule comprising a compound of the invention, a derivative or a salt thereof.

In another embodiment the invention provides the above described compound, a derivative or a salt thereof for use in a therapeutic, diagnostic, surgery or analytical method.

The method is selected from the group consisting of optical coherence tomography, fluorescence spectroscopy, fluorimetry, fluorescence lifetime, fluorescence microscopy, fluorescence tomography, whole-body fluorescence imaging, flow cytometry, fluorescence-assisted cell sorting, fluorescence-guided surgery, fluorescence endomicroscopy, multi-spectral optoacoustic imaging, Raman spectroscopy, Raman imaging, fundus camera imaging and angiography.

Preferably, the method comprises labelling, tracking, and/or imaging biomolecules, cells and tissues in vivo, in vitro or ex vivo. More preferably in vivo.

Conveniently, the method is fluorescence-guided surgery of cancer.

Further, the method may be fluorescent probes for the diagnosis of pathogenic protein aggregates in neurodegenerative diseases.

A further embodiment of the invention relates to a diagnostic method comprising administering (e.g. local or systemic administration) to an organism, preferably a mammal dye-labelled agents or dye-labelled cells associated to disease biomarkers (e.g. immune cells, dead cells, cancer cells) comprising a compound of formula (I), and identifying them with an optical readout by an appropriate technique (e.g. optical coherence tomography, fluorescence spectroscopy, fluorimetry, fluorescence lifetime, fluorescence microscopy, flow cytometry, fluorescence-assisted cell sorting, fluorescence-guided surgery, fluorescence endomicroscopy, multi-spectral optoacoustic imaging, Raman spectroscopy, Raman imaging or angiography) in a relevant biological sample (e.g. blood, biopsy, tissue, lavage) in order to diagnose a diseased state or stratify patients according to different disease states.

The present invention also provides surgery methods comprising the steps of administration to a mammal a dye-labelled agents or dye-labelled cells (e.g. local or systemic administration), identification of an optical readout by an appropriate imaging modality (e.g. optical coherence tomography, fluorescence spectroscopy, fluorimetry, fluorescence lifetime, fluorescence microscopy, flow cytometry, fluorescence-assisted cell sorting, fluorescence-guided surgery, fluorescence endomicroscopy, multi-spectral optoacoustic imaging, Raman spectroscopy, Raman imaging or angiography) and subsequent choice of an appropriate surgical treatment, including fluorescence-guided surgery and ophthalmic surgical procedures.

The present invention further provides therapeutic methods comprising administration to a mammal of a compound of the invention, a derivative or a salt thereof linked to a molecule with biological activity (e.g. small molecule, peptide, protein, antibody, nanoparticle) to identify optimal administration routes and dosage by means of optical coherence tomography, fluorescence spectroscopy, fluorimetry, fluorescence lifetime, fluorescence microscopy, flow cytometry, fluorescence-assisted cell sorting, fluorescence-guided surgery, fluorescence endomicroscopy, multi-spectral optoacoustic imaging, Raman spectroscopy, Raman imaging or angiography.

The present invention also provides analytical method to characterize dye-labelled molecules by optical coherence tomography, fluorescence spectroscopy, fluorimetry, fluorescence lifetime, fluorescence microscopy, flow cytometry, fluorescence-assisted cell sorting, fluorescence-guided surgery, fluorescence endomicroscopy, multi-spectral optoacoustic imaging, Raman spectroscopy or Raman imaging.

Anyone of the methods described herewith may comprise labelling, tracking, or imaging biomolecules, cells and tissues in vivo, in vitro or ex vivo.

The present invention further provides a method for imaging of cells in vivo said method comprises the steps of administration of dye-labelled agents or dye-labelled cells (e.g. local or systemic administration) and identification of an optical readout by an appropriate imaging modality (e.g. optical coherence tomography, fluorescence spectroscopy, fluorescence-guided surgery, fluorescence endomicroscopy, multi-spectral optoacoustic imaging, Raman spectroscopy, Raman imaging or angiography).

The present invention further provides a pharmaceutical formulation comprising the compound of formula (I), a derivative or a salt thereof and a pharmaceutically acceptable carrier.

A pharmaceutically acceptable carrier may be for example physiological sterile saline solution, sterile water solution, pyrogen-free water solution, isotonic saline solution, and phosphate buffer solution.

The present invention further provides the pharmaceutical formulation comprising the compound of formula (I), a derivative or a salt thereof and a pharmaceutically acceptable carrier for use in the therapeutic, diagnostic, surgery or analytical method described above.

The present invention further provides a kit said kit comprising the compound of the invention, a derivative or a salt thereof as described above as a labelling reagent for biomolecules and/or cells, aqueous buffers and/or solvent for reconstitution, packaging materials and instructions for use thereof.

FIGURES

FIG. 1 shows the solvatochromic properties of SCOTfluor-76, 78, 79, 80, 81 and of NBD. All compounds were dissolved in different organic solvents, including toluene, chloroform, tetrahydrofuran, ethanol, DMSO and water (final concentrations: 10-50 µM). Fluorescence spectra were acquired on a spectrophotometer upon excitation at their maxima absorbance wavelengths.

Figure 2:
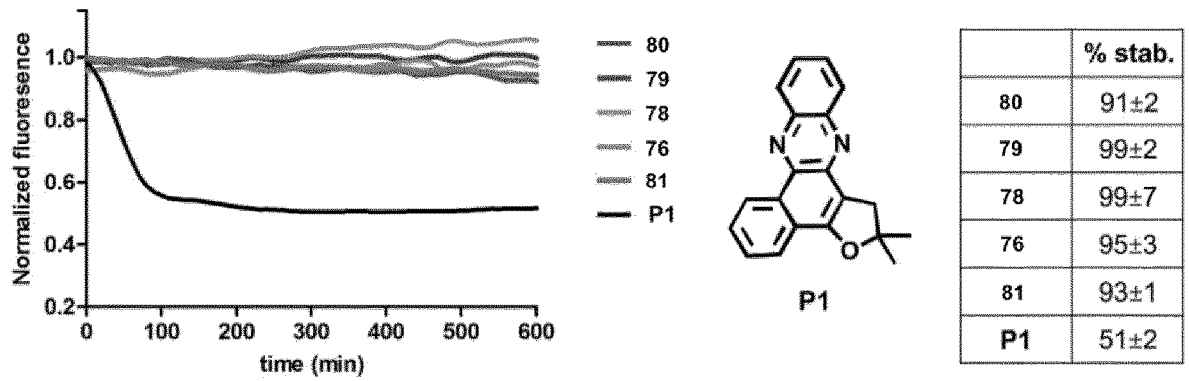

FIG. 2 shows the photostability of SCOTfluor-76, 78, 79, 80, 81 compared to P1. All compounds were dissolved in DMSO:water (1:99) (final concentrations: 10-50 µM). Time-course fluorescence emission for up to 10 h were acquired on a spectrophotometer upon excitation at their maxima absorbance wavelengths.

Figure 3:
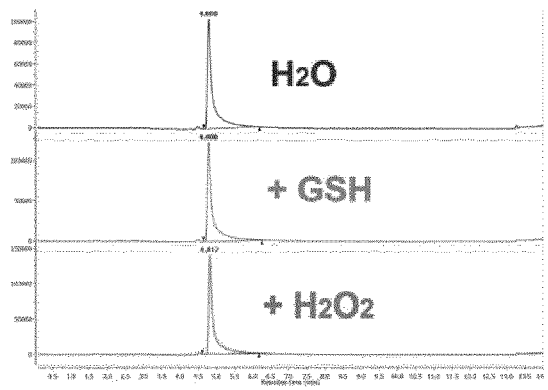
Figure 3:
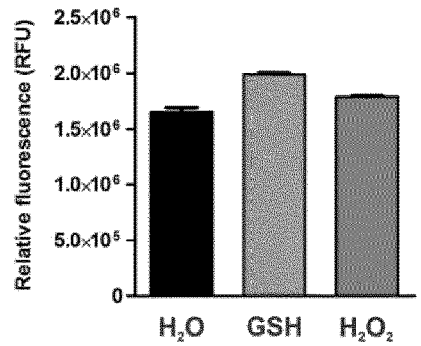
Figure 3:
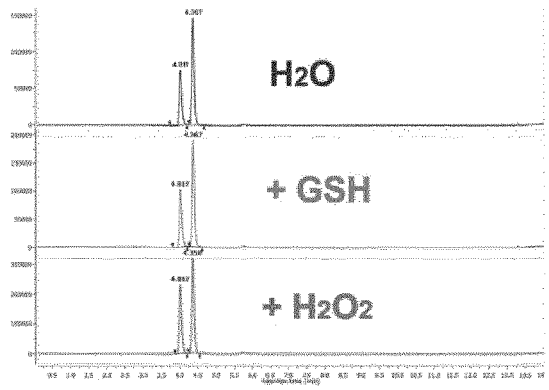
Figure 3:
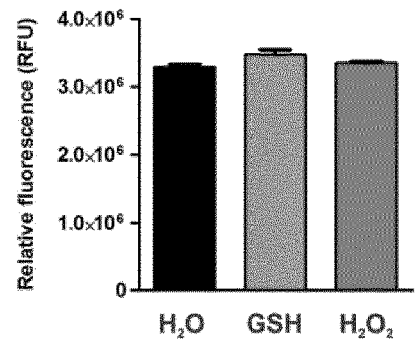

FIG. 3 shows the chemical stability to physiological and oxidative conditions of SCOTfluor-84 and 90. Compounds were diluted in pure water or aqueous buffers containing glutathione (1 mM) or hydrogen peroxide (100 µM).

Samples were incubated for 1 h at r.t. and analysed by reverse-phase liquid chromatography and mass spectrometry.

Figure 4:
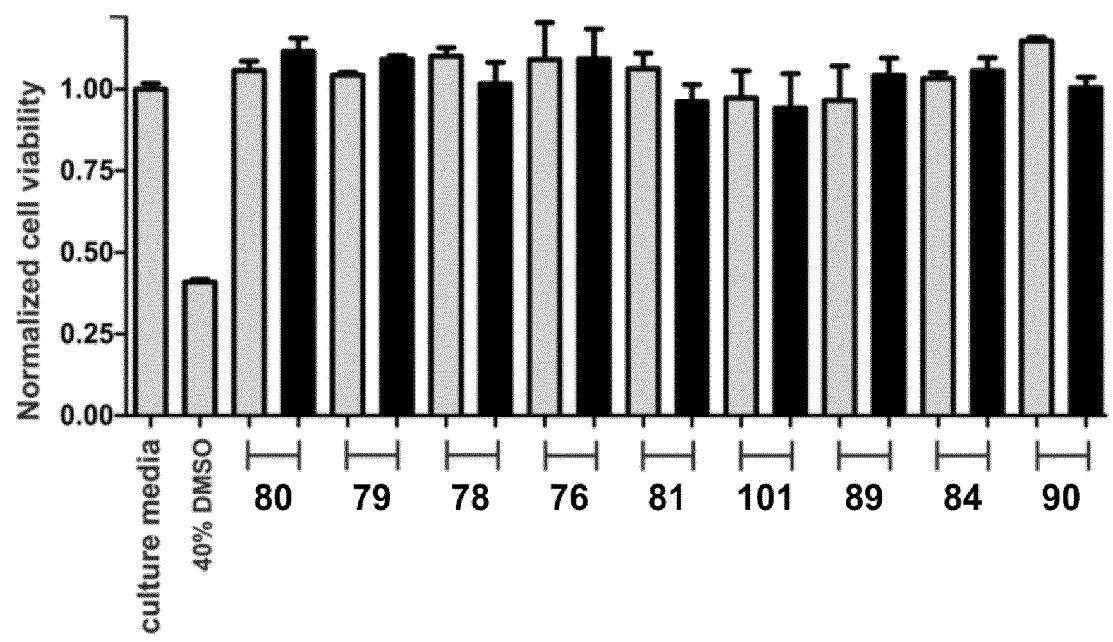

FIG. 4 shows the cytotoxicity assay of compounds SCOTfluor-76, 78, 79, 80, 81, 84, 89, 90, 101 in HeLa human cancer cells.

FIG. 5A) shows NIR-fluorescent ceramide SCOTfluor-101; B) Emission of SCOTfluor-101 in PBS (black) and in phosphatidylcholine:cholesterol (7:1) liposomes (red). C) Time-lapse confocal microscopy images of A549 cells treated with SCOTfluor-101 (50 µM, red), LysoTracker Blue (magenta) and ER Tracker Green (green) after 15 min (co-localization: white arrows) and 3 h (co-localization: yellow arrows). Total co-localization coefficients (R) were determined using ImageJ. Scale bar: 15 µm.

Figure 6:
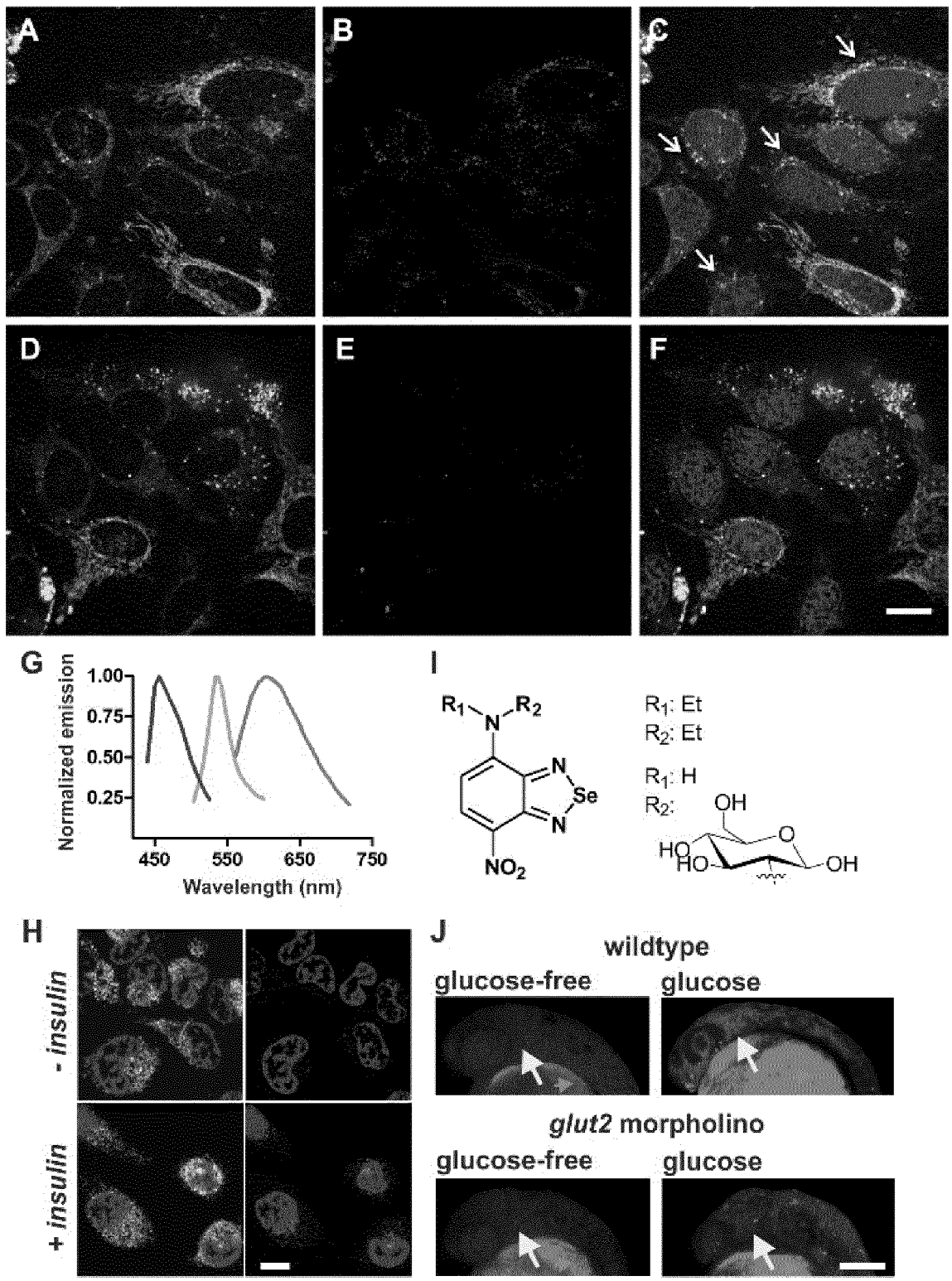

FIG. 6 shows fluorescence images of GLUT4-EGFP HeLa cells treated with compound SCOTfluor-89. A-F) Green (GLUT4-EGFP), red (SCOTfluor-89, 100 µM) and merged (Hoechst 33342) images of HeLa cells without additional glucose (A-C) and in media containing 5 mM D-glucose (A-F). White arrows identify co-localization of GLUT4-EGFP and SCOTfluor-89. Scale bar: 10 µm. G) Fluorescence emission spectra of BFP (blue), GFP (green) and SCOTfluor-89 (red). H) Insulin-dependent (100 nM, 1 h) uptake of SCOTfluor-89 (red, 100 µM) in GLUT4-EGFP HeLa cells. I) Chemical structures of compounds SCOTfluor-54 and SCOTfluor-89. J) In vivo images of the head in zebrafish embryos (28 hpf) after injection of SCOTfluor-54 or SCOTfluor-89 (both 50 pmol) to the yolk sac (blue arrowheads). Fluorescence images were taken of wildtype zebrafish or zebrafish that had been injected at one cell stage with 4.2 ng anti-sense glut2 morpholino. Yellow arrows point at midbrain and hindbrain regions within the zebrafish embryo heads. Scale bar: 100 µm.

Figure 7:
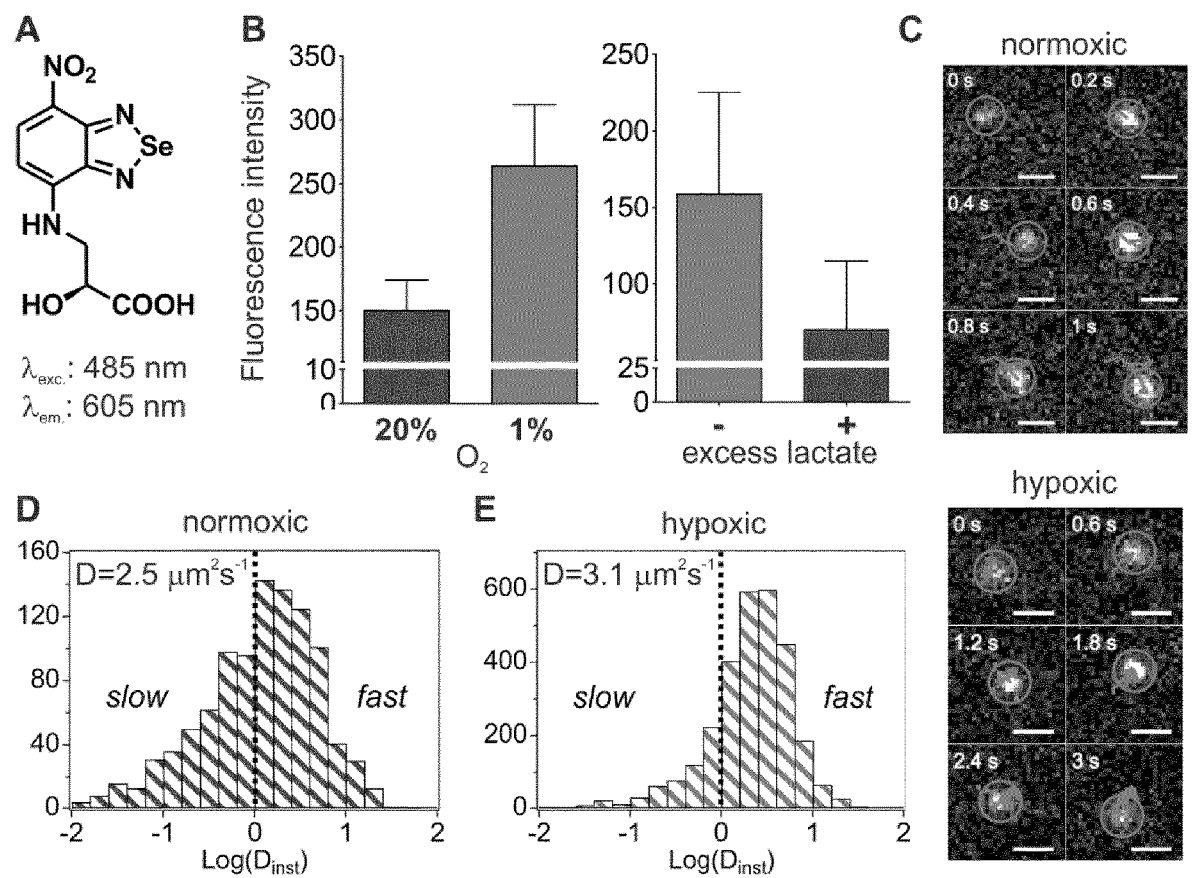

FIG. 7 shows A) Structure of compound SCOTfluor-84. B) Fluorescence emission of live cells after incubation with compound SCOTfluor-84 (100 µM) at different oxygen tensions (normoxia: blue; hypoxia: red) and in normoxic cells after competition with lactic acid (no lactate: red; 5 mM lactate: blue). Values as means and s.e.m as error bars. C) Time-lapse TIRF tracking of fluorescent particles in untreated (top) and DMOG-treated (10 µM, bottom) HeLa cells after incubation with compound SCOTfluor-84 (100 µM). Scale bars: 1 µm. D) Histograms of the diffusion coefficients of fluorescent particles in normoxic (blue) and hypoxic (red) cells. Dotted lines delineate fast and slow diffusion species. Mean diffusion coefficients (D) were determined after averaging the tracks of multiple particles for each condition (n=1,009 for untreated; n=2,906 for DMOG-treated).

Figure 8:
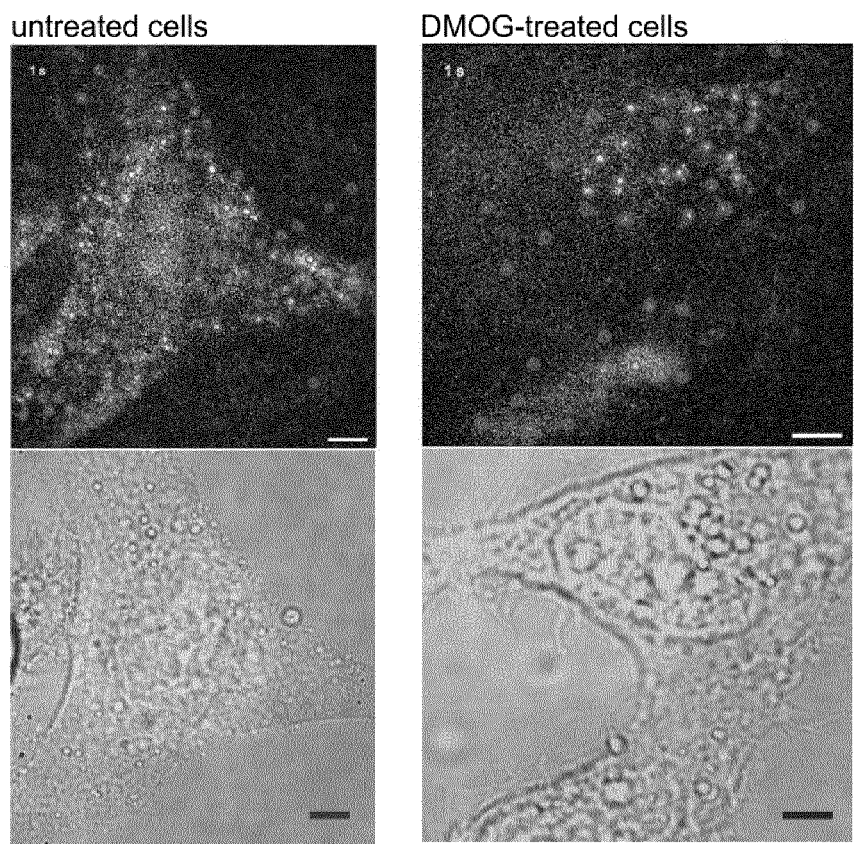

FIG. 8 shows fluorescence emission of live cells after incubation with SCOTfluor-84 (100 µM) at different oxygen tensions (normoxia: left; hypoxia: right) and in normoxic cells after competition with lactic acid (no lactate: left; with 5 mM lactate: right). Values as means and s.e.m as error bars. C) Time-lapse TIRF tracking of fluorescent particles in untreated (top) and DMOG-treated (10 µM, bottom) HeLa cells after incubation with compound SCOTfluor-84 (100 µM). Scale bars: 1 µm. Histograms of the diffusion coefficients of fluorescent particles in normoxic (left) and hypoxic (right) cells. Dotted lines delineate fast and slow diffusion species. Mean diffusion coefficients were determined after averaging the tracks of multiple particles for each condition (n=1,009 for untreated; n=2,906 for DMOG-treated).

Figure 9:
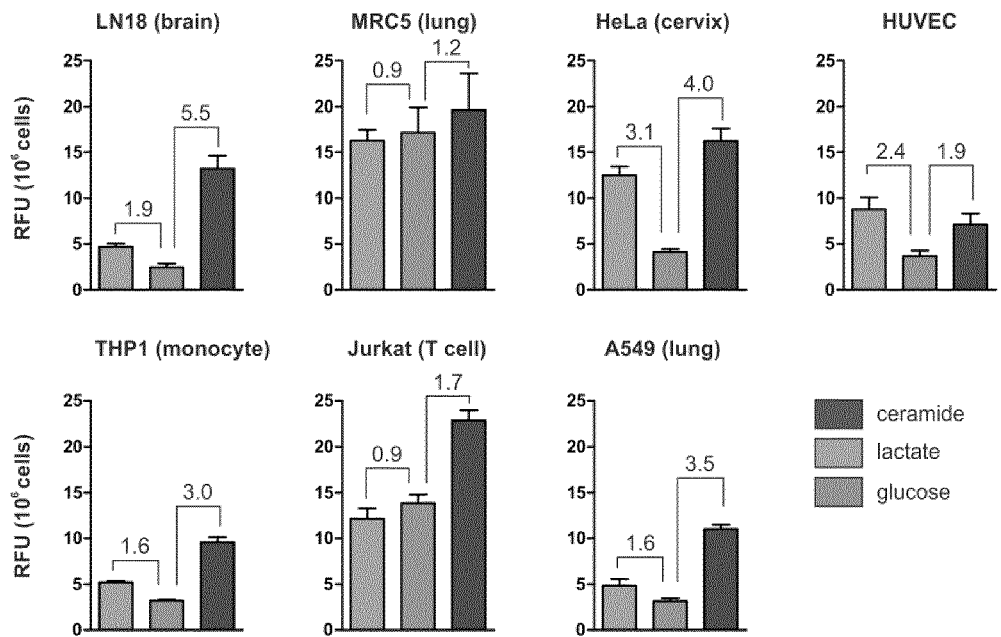

FIG. 9 shows the fluorescence intensities of SCOTfluor-101, 84 and 90 as respective analogues of ceramide, lactic acid and glucose measured in different human cell lines. Values are presented as fluorescence emission per $10^6$ cells after normalization against the fluorescence intensity of the respective solutions in aqueous buffer. Fluorescence fold ratios glucose vs. lactate (left) and ceramide vs. lactate (right) are calculated for cell type. Data presented as means and s.e.m as error bars.

DEFINITIONS

As used herein, the term "derivative" is used to refer to the residue of a chemical compound, such as an amino acid, after it has undergone chemical modification. For instance, these could include derivatives incorporating linkers with reactive groups for bioconjugation (e.g. amines, carboxylic acids, succinimidyl esters, maleimides, azides, alkynes, tetrazines), as well as derivatives of antibodies, proteins, peptides and small molecules.

As used herein, the term "salt" is used to refer to an assembly of cations and anions. These could include sodium, ammonium, quaternary ammonium, calcium, magnesium and potassium as cations or iodine, chloride, bromide, formate, perchlorate, hydrochlorate, sulfate, hydroxide, phosphate and trifluoroacetate as anions. The salt may only include the compound or the derivative of the invention and an anion. The salt may also include additional cations and anions. Preferred cations are of sodium and ammonium. Preferred anions are of iodine, bromide, formate and trifluoroacetate.

The compounds of the invention and listed above include stereoisomeric mixtures as well as single enantiomers or diastereoisomers. Preferably the compounds are (S)-enantiomers for amino acids, (D)-glucose and (L)-lactic acid.

Examples

The preparation of SCOTfluors was achieved in two synthetic steps from a common intermediate of formula II. The detailed preparation of the Scotfluors is described below as well as the analytical methods used in the examples.

General Materials

Commercially available reagents were used without further purification. Thin-layer chromatography was conducted on Merck silica gel 60 F254 sheets and visualized by UV (254 and 365 nm). Silica gel (particle size 35-70 µm) was used for column chromatography. $^1$H and $^{13}$C spectra were recorded in a Bruker Avance 500 spectrometer (at 500 and 126 MHz, respectively). Data for $^1$H NMR spectra are reported as chemical shift δ (ppm), multiplicity, coupling constant (Hz), and integration. Data for $^{13}$C NMR spectra are reported as chemical shifts relative to the solvent peak. HPLC-MS analysis was performed on a Waters Alliance 2695 separation module connected to a Waters PDA2996 photo-diode array detector and a ZQ Micromass mass spectrometer (ESI-MS) with a Phenomenex column ($C_{18}$, 5 µm, 4.6×150 mm). Conjugates were purified using a Waters semipreparative HPLC system using a Phenomenex column ($C_{18}$ Axial, 10 µm, 21.2×150 mm) and UV detection.

Synthesis of Nitrobenzotriazoles (SCOTfluor-5, SCOTfluor-6)

To a solution of 3-chloro or 3-fluoro-6-nitrobenzene-1,2-diamine (0.16 mmol) in $H_2O$:AcOH (10:1, 2 mL) was added $NaNO_2$ (0.22 mmol) and the reaction was stirred for 30 min at r.t. Then, the mixture was extracted with EtOAc (2×30 mL), washed with 2 M HCl (10 mL), $NaHCO_{3(aq)}$ (10 mL) and brine (10 mL), dried over $MgSO_4$ and the solvent was removed under reduced pressure to give a light brown solid, which was purified by column chromatography (EtOAc: Hexane 6:4).

4-chloro-7-nitro-2H-benzo[d][1,2,3]triazole (98% yield, yellow solid) $^1$H NMR (500 MHz, DMSO-$d_6$) δ 8.45 (d, J=8.4 Hz, 1H), 7.75 (d, J=8.4 Hz, 1H). $^{13}$C NMR (126 MHz, DMSO-$d_6$) δ 144.6, 133.0, 131.9, 128.2, 125.5, 124.1. m/z (ESI): calcd for $C_6H_4ClN_4O_2^+$ [M+H]$^+$: 199.0, found: 199.6.

4-fluoro-7-nitro-2H-benzo[d][1,2,3]triazole (66% yield, yellow solid) $^1$H NMR (500 MHz, DMSO-$d_6$) δ 8.55 (dd, J=8.7, 3.9 Hz, 1H), 7.50 (dd, J=9.7, 8.7 Hz, 1H). $^{13}$C NMR (126 MHz, DMSO-$d_6$) δ 158.0, 155.9, 136.6, 130.6, 127.3 (d, $J_{C-F}$=9.7 Hz), 109.7 (d, $J_{C-F}$=20.1 Hz). m/z (ESI): calcd for $C_6H_4FN_4O_2^+$ [M+H]$^+$: 183.0, found: 183.5.

Synthesis of Benzothiadiazoles (SCOTfluor-161, SCOTfluor-162)

To a solution of 3-chloro or 3-fluoro-6-nitrobenzene-1,2-diamine (0.7 mmol) in toluene (1 mL), PhNSO (5.0 mmol) was added and the reaction was heated at 120° C. for 5 h. Then, the solvent was removed under reduced pressure and the crude was purified by column chromatography (EtOAc: Hexane 4:6).

4-chloro-7-nitrobenzo[c][1,2,5]thiadiazole (65% yield, yellow solid) $^1$H NMR (500 MHz, DMSO-$d_6$) δ 8.69 (d, J=8.2 Hz, 1H), 8.12 (d, J=8.2 Hz, 1H). $^{13}$C NMR (126 MHz, DMSO-$d_6$) δ 153.2, 146.6, 138.7, 132.4, 128.8, 128.1. m/z (ESI): calcd for $C_6H_2ClN_3O_2S^+$ [M]$^+$: 214.9, found: 214.9.

4-fluoro-7-nitrobenzo[c][1,2,5]thiadiazole (68% yield, yellow solid) $^1$H NMR (500 MHz, DMSO-$d_6$) δ 8.80 (dd, J=8.5, 4.5 Hz, 1H), 7.79 (dd, J=9.4, 8.6 Hz, 1H). $^{13}$C NMR (126 MHz, DMSO-$d_6$) δ 157.3, 155.1, 148.4 (d, $J_{C-F}$=3.6 Hz), 146.3 (d, $J_{C-F}$=15.7 Hz), 136.5, 130.5 (d, $J_{C-F}$=9.9 Hz), 112.3 (d, $J_{C-F}$=19.5 Hz). m/z (ESI): calcd for $C_6H_2FN_3O_2S^+$ [M]$^+$: 199.0, found: 199.0.

Synthesis of 4-Chloro and 4-Fluorobenzoselenadiazoles (SCOTfluor-1, SCOTfluor-2)

SeO$_2$ (4.5 mmol) was added to a solution of 3-chlorobenzene-1,2-diamine or 3-fluorobenzene-1,2-diamine (3.7 mmol) in EtOH (20 mL) and the reaction was refluxed for 30 min. Then, the solvent was removed under reduced pressure and the crude products were purified by column chromatography (Hexane:EtOAc 7:3).

4-chlorobenzo[c][1,2,5]selenadiazole (91% yield, white solid) $^1$H NMR (500 MHz, DMSO-$d_6$) δ 7.84 (dd, J=9.0, 1.0 Hz, 1H), 7.70 (dd, J=7.1, 0.9 Hz, 1H), 7.53 (dd, J=9.0, 7.1 Hz, 1H). $^{13}$C NMR (126 MHz, DMSO-$d_6$) δ 160.2, 156.8, 129.7, 128.5, 126.9, 123.0. m/z (ESI): calcd for $C_6H_4ClN_2Se^+$ [M+H]$^+$: 218.9, found: 218.9.

4-fluorobenzo[c][1,2,5]selenadiazole (90% yield, white solid) $^1$H NMR (500 MHz, CDCl$_3$) δ 7.69 (ddd, J=9.2, 0.8, 0.4 Hz, 1H), 7.47 (ddd, J=9.1, 7.3, 5.2 Hz, 1H), 7.10 (ddd, J=10.1, 7.3, 0.9 Hz, 1H). $^{13}$C NMR (126 MHz, CDCl$_3$) δ 155.0, 145.2, 129.0, 123.4, 119.6 (d, J=5.5 Hz), 111.0 (d, J=17.0 Hz). m/z (ESI): calcd for $C_6H_4FN_2Se^+$ [M+H]$^+$: 202.9, found: 202.9.

General Procedure for the Synthesis of Nitrobenzoselenadiazoles (SCOTfluor-3, SCOTfluor-4)

4-Chloro or 4-fluorobenzoselenadiazole (2.3 mmol) was dissolved in H$_2$SO$_4$ (5 mL) and HNO$_3$ (1.5 mL) was added dropwise at 0° C. After 15 min, the reaction was quenched by dropwise addition of H$_2$O (100 mL), leading to the formation of a yellow precipitate. The organic phase was extracted with EtOAc (3×150 mL) and dried over anhydrous MgSO$_4$. The solvent was removed under reduced pressure and the crude product was purified by column chromatography (Hexane:EtOAc 4:6).

4-chloro-7-nitrobenzo[c][1,2,5]selenadiazole (97% yield, yellow solid) $^1$H NMR (500 MHz, DMSO-$d_6$) δ 8.49 (d, J=8.0 Hz, 1H), 7.93 (d, J=8.0 Hz, 1H). $^{13}$C NMR (126 MHz, DMSO-$d_6$) δ 157.2, 150.6, 140.3, 133.6, 127.8, 126.5. m/z (ESI): calcd for $C_6H_3ClN_3O_2Se^+$ [M+H]$^+$: 263.9, found: 263.9.

4-fluoro-7-nitrobenzo[c][1,2,5]selenadiazole (89% yield, yellow solid) $^1$H NMR (500 MHz, DMSO-$d_6$) δ 8.61 (dd, J=8.4, 4.7 Hz, 1H), 7.55 (dd, J=9.7, 8.4 Hz, 1H). $^{13}$C NMR (126 MHz, DMSO-$d_6$) δ 157.7, 155.5, 152.3 (d, $J_{C-F}$=2.9 Hz), 133.2, 129.5 (d, $J_{C-F}$=10.0 Hz), 110.1 (d, $J_{C-F}$=20.4 Hz). m/z (ESI): calcd for $C_6H_3FN_3O_2Se^+$ [M+H]$^+$: 247.9, found: 247.7.

Synthesis of C-Bridged Benzoimidazoles (SCOTfluor-7, SCOTfluor-8, SCOTfluor-9, SCOTfluor-10)

To a solution of 3-chloro or 3-fluoro-6-nitrobenzene-1,2-diamine (0.3 mmol) in EtOH (5 mL), Cu(OAc)$_2$ (0.015 mmol) was added followed by the corresponding ketone (30 mmol). The resulting mixture was heated at 80° C. overnight. Then, the reaction mixture was filtered through Celite and the solvent was removed under reduced pressure to give crude products, which were purified by column chromatography (DCM:Hexane 1:1).

4-chloro-2,2-dimethyl-7-nitro-2H-benzo[d]imidazole (82% yield, red solid) $^1$H NMR (500 MHz, CDCl$_3$) δ 7.25 (d, J=9.4 Hz, 1H), 6.46 (d, J=9.4 Hz, 1H), 1.66 (s, 6H). $^{13}$C NMR (126 MHz, CDCl$_3$) δ 138.6, 138.0, 132.2, 126.6, 117.9, 114.0, 80.9, 30.7. m/z (ESI): calcd for $C_6H_9ClN_3O_2^+$ [M+H]$^+$: 226.0, found: 226.5.

4-fluoro-2,2-dimethyl-7-nitro-2H-benzo[d]imidazole (79% yield, red solid) $^1$H NMR (500 MHz, CDCl$_3$) δ 7.33 (dd, J=9.6, 4.6 Hz, 1H), 6.35 (dd, J=9.6, 9.1 Hz, 1H), 1.64 (s, 6H). $^{13}$C NMR (126 MHz, CDCl$_3$) δ 150.3, 148.3, 141.4 (d, $J_{C-F}$=11.3 Hz), 126.4 (d, $J_{C-F}$=17.0 Hz), 115.3 (d, $J_{C-F}$=8.4 Hz), 107.3 (d, $J_{C-F}$=22.1 Hz), 81.8, 30.6. m/z (ESI): calcd for $C_6H_9FN_3O_2^+$ [M+H]$^+$: 210.1, found: 209.8.

4-chloro-7-nitrospiro[benzo[d]imidazole-2,1'-cyclohexane] (94% yield, red solid) $^1$H NMR (500 MHz, Methanol-$d_4$) δ 7.08 (d, J=9.4 Hz, 1H), 6.36 (d, J=9.4 Hz, 1H), 1.89-1.81 (m, 4H), 1.73 (m, 4H), 1.64-1.56 (m, 2H). $^{13}$C NMR (126 MHz, Methanol-$d_4$) δ 139.4, 139.0, 125.4, 117.1, 112.6, 111.8, 82.6, 38.9, 24.4, 22.2. m/z (ESI): calcd for $C_{12}H_{13}ClN_3O_2^+$ [M+H]$^+$: 266.0, found: 266.4.

4-fluoro-7-nitrospiro[benzo[d]imidazole-2,1'-cyclohexane] (80% yield, red solid) 1H NMR (500 MHz, Methanol-$d_4$) δ 7.17 (dd, J=9.6, 4.5 Hz, 1H), 6.30 (t, J=9.5 Hz, 1H), 1.93-1.86 (m, 4H), 1.70 (ddt, J=9.7, 6.4, 3.0 Hz, 4H), 1.66-1.57 (m, 2H). $^{13}$C NMR (126 MHz, Methanol-$d_4$) δ 149.0, 147.1, 142.0 (d, $J_{C-F}$=11.9 Hz), 127.6 (d, $J_{C-F}$=17.1 Hz), 124.4, 112.9 (d, $J_{C-F}$=8.4 Hz), 106.4 (d, $J_{C-F}$=22.9 Hz), 83.4, 38.8, 24.4, 22.3. m/z (ESI): calcd. for $C_{12}H_{12}FN_3O_2^+$ [M+H]$^+$: 250.1, found: 250.3.

General Procedure for Amine Incorporation

To a solution of SCOTfluor-4, 6 or 162 (0.04 mmol) in MeCN (1 mL) were added triethylamine (0.06 mmol) as well as N-propylamine or N,N-diethylamine (0.06 mmol). The mixture was stirred at r.t. until TLC monitoring showed complete consumption of the starting material. Volatiles were removed under reduced pressure and the crude was purified by column chromatography (DCM:MeOH 98:2).

N,N-diethyl-7-nitro-2H-benzo[d][1,2,3]triazol-4-amine (28% yield, yellow solid) $^1$H NMR (500 MHz, Methanol-$d_4$) δ 8.62 (d, J=9.4 Hz, 1H), 6.64 (d, J=9.4 Hz, 1H), 4.10 (q, J=7.1 Hz, 4H), 1.42 (t, J=7.1 Hz, 6H). $^{13}$C NMR (126 MHz, Methanol-$d_4$) δ 150.1, 147.2, 146.2, 132.7, 126.3, 102.7, 29.4, 11.7. m/z (ESI): calcd for $C_{10}H_{14}N_5O_2^+$ [M+H]$^+$: 236.1, found: 236.2.

7-nitro-N-propyl-2H-benzo[d][1,2,3]triazol-4-amine (17% yield, yellow solid) $^1$H NMR (500 MHz, Methanol-$d_4$) δ 8.24 (d, J=9.0 Hz, 1H), 6.50 (d, J=9.1 Hz, 1H), 3.75-3.43 (m, 2H), 1.88-1.72 (m, 2H), 1.08 (t, J=7.4 Hz, 3H). $^{13}$C NMR (126 MHz, Methanol-$d_4$) δ 152.9, 140.3, 134.5, 128.3, 120.7, 100.4, 29.4, 22.0, 10.3. m/z (ESI): calcd for $C_6H_{12}N_5O_2^+$ [M+H]$^+$: 221.1, found: 221.3.

N,N-diethyl-7-nitrobenzo[c][1,2,5]thiadiazol-4-amine (93% yield, orange solid) $^1$H NMR (500 MHz, Methanol-$d_4$) δ 8.62 (d, J=9.4 Hz, 1H), 6.64 (d, J=9.4 Hz, 1H), 4.10 (q, J=7.1 Hz, 4H), 1.42 (t, J=7.1 Hz, 6H). $^{13}$C NMR (126 MHz, Methanol-$d_4$) δ 150.1, 147.2, 146.2, 132.8, 126.3, 102.7, 29.3, 11.7. m/z (ESI): calcd for $C_{10}H_{13}N_4O_2S^+$ [M+H]$^+$: 253.1, found: 253.2.

7-nitro-N-propylbenzo[c][1,2,5]thiadiazol-4-amine (90% yield, orange solid) $^1$H NMR (500 MHz, Methanol-$d_4$) δ 8.67 (d, J=9.0 Hz, 1H), 6.54 (d, J=8.9 Hz, 1H), 3.51 (t, J=7.2 Hz, 2H), 1.90-1.77 (m, 2H), 1.08 (t, J=7.4 Hz, 3H). $^{13}$C NMR (126 MHz, Methanol-$d_4$) δ 148.4, 147.6, 146.7, 134.2, 126.7, 98.7, 44.6, 21.5, 10.3. m/z (ESI): calcd for $C_9H_{11}N_4O_2S^+$ [M+H]$^+$: 239.0, found: 238.8.

N,N-diethyl-7-nitrobenzo[c][1,2,5]selenadiazol-4-amine (70% yield, red solid) $^1$H NMR (500 MHz, DMSO-$d_6$) δ 8.50 (d, J=9.4 Hz, 1H), 6.47 (d, J=9.4 Hz, 1H), 4.01 (q, J=7.0 Hz, 4H), 1.32 (t, J=7.0 Hz, 6H). $^{13}$C NMR (126 MHz, DMSO-$d_6$) δ 153.9, 152.4, 148.7, 134.1, 128.2, 101.9, 47.8, 13.2. m/z (ESI): calcd for $C_{10}H_{12}N_4O_2SeNa^+$ [M+Na]$^+$: 323.0, found: 323.1.

7-nitro-N-propylbenzo[c][1,2,5]selenadiazol-4-amine (72% yield, red solid) $^1$H NMR (500 MHz, DMSO-$d_6$) δ 8.58 (d, J=9.0 Hz, 1H), 6.39 (d, J=9.0 Hz, 1H), 3.42 (q, J=6.8 Hz, 2H), 1.80-1.63 (m, 2H), 0.95 (t, J=7.4 Hz, 3H). $^{13}$C NMR (126 MHz, DMSO) δ 152.6, 152.4, 149.1, 135.9, 128.4, 97.7, 45.0, 21.8, 11.8. m/z (ESI): calcd for $C_6H_{11}N_4O_2Se^+$ [M+H]$^+$: 287.0, found: 286.8.

To a solution of SCOTfluor-8 or 10 (0.05 mmol) in MeCN (1 mL), NaHCO$_3$ (0.13 mmol) in H$_2$O was added, followed by N-propylamine or N,N-diethylamine (0.05 mmol) and the reaction was heated at 65° C. for 3 h. The reaction mixture was acidified with 0.2 N HCl and extracted with EtOAc. The organic layer was dried over anhydrous MgSO$_4$, the solvent was removed under reduced pressure and the crude product was purified by column chromatography (DCM:MeOH 95:5).

N,N-diethyl-2,2-dimethyl-7-nitro-2H-benzo[d]imidazol-4-amine (80% yield, purple solid) $^1$H NMR (500 MHz, Methanol-$d_4$) δ 8.46 (d, J=9.4 Hz, 1H), 6.00 (d, J=9.4 Hz, 1H), 4.06 (m, 4H), 1.61 (s, 6H), 1.35 (t, J=7.1 Hz, 6H). $^{13}$C NMR (126 MHz, Methanol-$d_4$) δ 155.3, 152.2, 150.6, 143.2, 124.4, 104.9, 99.4, 21.2, 11.3. m/z (ESI): calcd for $C_{13}H_{19}N_4O_2^+$ [M+H]$^+$: 263.1, found: 263.1.

2,2-dimethyl-7-nitro-N-propyl-2H-benzo[d]imidazol-4-amine (41% yield, purple solid) 1H NMR (500 MHz, Methanol-$d_4$) δ 8.52 (d, J=10.0 Hz, 1H), 5.75 (d, J=10.0 Hz, 1H), 2.76 (t, J=7.3 Hz, 2H), 1.67-1.57 (m, 2H), 1.56 (s, 6H), 0.99 (t, J=7.4 Hz, 3H). $^{13}$C NMR (126 MHz, Methanol-d4) δ 180.7, 158.6, 154.3, 145.5, 110.2, 103.0, 42.0, 22.9, 21.9, 9.9. m/z (ESI): calcd for $C_{12}H_{17}N_4O_2^+$ [M+H]$^+$: 249.1, found: 249.2.

6-((2,2-dimethyl-7-nitro-2H-benzo[d]imidazol-4-yl) amino)hexanoic acid (40% yield, purple solid) $^1$H NMR (500 MHz, Methanol-$d_4$) δ 8.53 (d, J=8.9 Hz, 1H), 5.93 (d, J=9.0 Hz, 1H), 3.49 (t, J=7.2 Hz, 2H), 2.32 (t, J=7.4 Hz, 2H), 1.78 (p, J=7.4 Hz, 2H), 1.75-1.64 (m, 2H), 1.60 (s, 6H), 1.53-1.42 (m, 2H). $^{13}$C NMR (126 MHz, Methanol-$d_4$) δ 176.9, 155.1, 151.6, 151.0, 145.0, 125.5, 105.6, 95.5, 43.1, 34.1, 27.7, 26.2, 24.6, 21.1. m/z (HRMS ESI): calcd for $C_{15}H_{21}N_4O_4^+$ [M+H]$^+$: 321.1561, found: 321.1557.

N,N-diethyl-7-nitrospiro[benzo[d]imidazole-2,1'-cyclohexan]-4-amine (38% yield, purple solid) $^1$H NMR (500 MHz, Methanol-$d_4$) δ 8.45 (d, J=9.4 Hz, 1H), 6.02 (d, J=9.4 Hz, 1H), 4.06 (m, 4H), 2.34 (td, J=12.3, 4.5 Hz, 4H), 2.11-1.88 (m, 4H), 1.75-1.58 (m, 2H), 1.36 (t, J=7.1 Hz, 6H). $^{13}$C NMR (126 MHz, Methanol-$d_4$) δ 155.3, 151.9, 150.5, 142.9, 124.4, 107.7, 99.4, 34.2, 33.3, 25.2, 24.5, 23.6, 11.5. m/z (ESI): calcd for $C_{16}H_{23}N_4O_2^+$ [M+H]$^+$: 303.2, found: 303.2.

7-nitro-N-propylspiro[benzo[d]imidazole-2,1'-cyclohexan]-4-amine (25% yield, purple solid) $^1$H NMR (500 MHz, Methanol-$d_4$) δ 8.53 (d, J=8.9 Hz, 1H), 5.95 (d, J=9.0 Hz, 1H), 3.45 (t, J=7.3 Hz, 2H), 2.07-1.90 (m, 4H), 1.78 (m, J=7.4 Hz, 2H), 1.72-1.60 (m, 4H), 1.33-1.22 (m, 2H), 1.05 (t, J=7.4 Hz, 3H). $^{13}$C NMR (126 MHz, Methanol-$d_4$) δ 155.1, 151.4, 144.6, 125.6, 108.5, 95.6, 44.9, 32.9, 25.1, 24.2, 21.4, 10.3. m/z (ESI): calcd for $C_{15}H_{21}N_4O_2^+$ [M+H]$^+$: 289.1, found: 289.1.

Synthesis of Lipid Analog SCOTfluor-101

To a solution of SCOTfluor-100 (5 mg, 0.016 mmol) in DMF:DCM (1:4, 0.5 mL), COMU (8.4 mg, 0.019 mmol) was added. After 5 min of stirring at r.t., sphingosine (6 mg, 0.019 mmol) dissolved in DMF:DCM (1:4, 0.4 mL) was added, followed by DIPEA (3.6 μL, 0.019 mmol). After stirring for 15 min at r.t. under N$_2$, the mixture was poured into H$_2$O:DCM (1:1, 8 mL) and the organic phase was washed with H$_2$O (2 mL), brine (2×2 mL) and dried over anhydrous MgSO$_4$. The solvent was removed under reduced pressure, and the product was isolated after column chromatography (gradient from pure DCM to DCM:MeOH, 95:5).

N-((2S,3R,E)-1,3-dihydroxyoctadec-4-en-2-yl)-6-((2,2-dimethyl-7-nitro-2H-benzo[d]imidazol-4-yl)amino)hexanamide (27% yield, purple solid) $^1$H NMR (500 MHz, Methanol-$d_4$) δ 8.53 (d, J=8.9 Hz, 1H), 5.92 (d, J=8.9 Hz, 1H), 5.77-5.64 (m, 1H), 5.52-5.41 (m, 1H), 4.38 (q, J=7.1 Hz, 1H), 3.80-3.64 (m, 2H), 3.57-3.50 (m, 2H), 2.26 (td, J=7.3, 1.8 Hz, 2H), 2.14-2.00 (m, 4H), 1.83-1.64 (m, 4H), 1.60 (s, 6H), 1.43-1.34 (m, 2H), 1.31 (s, 22H), 0.92 (t, J=6.9 Hz, 3H). $^{13}$C NMR (126 MHz, Methanol-$d_4$) δ 177.0, 155.2, 151.6, 151.0, 145.0, 133.3, 129.8, 125.5, 72.3, 65.3, 60.8, 55.4, 45.5, 43.1, 34.1, 32.0, 31.7, 29.4, 29.4, 29.3, 29.3, 29.2, 29.1, 29.0, 29.0, 28.9, 27.7, 26.2, 25.5, 25.1, 24.6, 22.3, 22.3, 21.1, 13.0.

m/z (HRMS ESI): calcd for $C_{33}H_{56}N_5O_5^+$ [M+H]$^+$: 602.4276, found: 602.4269.

Synthesis of Glucose SCOTfluor-89

To a solution of SCOTfluor-4 (10 mg, 0.04 mmol) in DMSO (1 mL), D-glucosamine hydrochloride (9 mg, 0.04 mmol) and triethylamine (17 μL, 0.12 mmol) were added, and the mixture was stirred at r.t. for 1.5 h. The mixture was poured into cold DCM and the precipitate was filtered and purified by semi-preparative HPLC.

(3R,4R,5S,6R)-6-(hydroxymethyl)-3-((7-nitrobenzo[c][1,2,5]selenadiazol-4-yl)amino)tetrahydro-2H-pyran-2,4,5-triol (90% yield, reddish solid) $^1$H NMR (500 MHz, DMSO-$d_6$) δ 8.58 (d, J=8.9 Hz, 1H), 7.06 (s, 1H), 6.61 (d, J=8.9 Hz, 1H), 5.20 (d, J=4.3 Hz, 2H), 5.09 (s, 1H), 4.52 (s, 1H), 3.77 (d, J=10.5 Hz, 1H), 3.70 (dd, J=10.3, 5.0 Hz, 1H), 3.61-3.53 (m, 1H). $^{13}$C NMR (126 MHz, DMSO-$d_6$) δ 152.1, 148.5, 135.6, 128.7, 99.0, 90.6, 73.3, 73.0, 70.8, 61.5, 58.3. m/z (HRMS ESI): calcd. for $C_{12}H_{15}N_4O_7Se^+$ [M+H]$^+$: 407.0092, found: 407.0100.

Synthesis of Lactic Acid SCOTfluor-84

To a solution of SCOTfluor-4 (20 mg, 0.08 mmol) in DMSO (0.5 mL) L-isoserine (17 mg, 0.16 mmol) was added, and the mixture was stirred at 50° C. for 4 h. The mixture was diluted with MeOH and purified by semi-preparative HPLC.

(R)-2-hydroxy-3-((7-nitrobenzo[c][1,2,5]selenadiazol-4-yl)amino)propanoic acid (38% yield, reddish solid) $^1$H NMR (500 MHz, DMSO-d$_6$) δ 8.60 (d, J=8.9, 1H), 7.99 (t, J=6.0, 1H), 6.48 (d, J=9.0, 1H), 4.38 (dd, J=7.2, 4.5, 1H), 3.82-3.59 (m, 2H). $^{13}$C NMR (126 MHz, DMSO-d$_6$) δ 174.2, 152.3, 148.7, 135.5, 129.0, 98.4, 69.1, 46.8, 40.9. m/z (HRMS ESI): calcd. for $C_9H_9N_4O_5Se^+$ [M+H]$^+$: 332.9727, found: 332.9769.

Synthesis of Glucose SCOTfluor-90

To a solution of SCOTfluor-162 (27 mg, 0.14 mmol) in MeCN (0.8 ml) was added D-glucosamine hydrochloride (35 mg, 0.16 mmol) in saturated $NaHCO_{3\ (aq)}$ (0.8 mL) and the reaction was stirred at 30° C. for 24 h. The solvent was removed under reduced pressure, and the product was isolated by normal phase chromatography (DCM:MeOH, 9:1).

(3R,4R,5S,6R)-6-(hydroxymethyl)-3-((7-nitrobenzo[c][1,2,5]thiadiazol-4-yl)amino)tetrahydro-2H-pyran-2,4,5-triol (13% yield, orange solid) $^1$H NMR (500 MHz, DMSO-d$_6$) δ 8.61 (d, J=7.4 Hz, 1H), 7.03 (s, 1H), 6.82 (d, J=7.4 Hz, 1H), 5.21 (s, 1H), 5.07-5.18 (m, 2H), 4.52 (t, 1H), 3.85-3.65 (m, 4H), 3.50-3.47 (m, 1H). $^{13}$C NMR (126 MHz, DMSO-d$_6$) δ 149.2, 146.6, 134.6, 125.7, 100.9, 95.81, 90.3, 77.1, 74.9, 72.6, 71.0, 61.4, 58.2. m/z (HRMS ESI): calcd. for $C_{12}H_{15}N_4O_7S^+$ [M+H]$^+$: 359.0656, found: 359.0687.

Cell Culture and Transfection

A549 and HeLa cells were obtained from LGC Standards and cultured in Dulbecco's modified Eagle's medium (DMEM) supplemented with 10% FBS, 100 U mL$^{-1}$ penicillin and 0.1 mg mL$^{-1}$ streptomycin. For transfection experiments, HeLa cells were transfected with pcDNA-PYP-GLUT4-HA-EGFP. Amplification of plasmid-DNA was performed by transformation of competent E. coli DH5a, followed by isolation of pcDNA-PYP-GLUT4-HA-EGFP using GeneJet Plasmid Miniprep kit (ThermoFisher) according to the manufacturer's instructions. Prior to transfection, pcDNA concentration was determined using Nano-Drop. Transfection of HeLa cells was performed according to manufacturer's protocol with 1 μg pcDNA-PYP-GLUT4-HA-EGFP using Lipofectamine 3000. Non-transfected as well as transfected cells were maintained at 37° C. and 5% $CO_2$ throughout the imaging experiments.

Live-Cell Fluorescence Microscopy

Confocal fluorescence microscopy was performed on a confocal Leica SP5 or a spinning disk microscope with excitation at 488 nm (ER Tracker, LysoTracker, EGFP & SCOTfluor-89), 561 nm (SCOTfluor-101) and 405 nm (Hoechst 33342). Prior to time-lapse imaging and imaging of HeLa cells, cells were incubated in Krebs-Ringer bicarbonate buffer (KRB) (129 mM NaCl, 4.7 mM KCl, 1.2 mM $KH_2PO_4$, 5 mM $NaHCO_3$, 10 mM HEPES; 2.5 mM $CaCl_2$, 1.2 mM $MgCl_2$ and 0.2% BSA, pH 7.4) at 37° C. for 3 h. When appropriate, HeLa cells were washed and imaged in KRB with 1 μM Hoechst 33342 at 37° C., 5% $CO_2$.

Isolation of Human Neutrophils and Flow Cytometry

Ex vivo experiments with fresh human peripheral blood from healthy donors were approved by the Accredited Medical Regional Ethics Committee (AMREC, reference number 15-HV-013). Peripheral blood polymorphonuclear cells from healthy volunteers were isolated as previously described. Briefly, citrated blood (3.8%) was centrifuged at room temperature at 350 g for 20 min, platelet-rich plasma was removed and separation from erythrocytes was achieved by Dextran sedimentation and fractionation of leukocytes using isotonic Percoll gradient. Polymorphonuclear leukocytes (>95% neutrophils) were harvested from the 70%-81% interfaces. Neutrophils were cultured in RPMI without glucose supplemented with penicillin/streptavidin. For experiments under hypoxic conditions, medium was pre-conditioned for at least 1 h at 1% $O_2$ at 37° C. Neutrophils were cultured in the absence or presence of 100 nM fMLP (Sigma-Aldrich) under hypoxic (1% $SpiO_2$, 37° C.) or normoxic (21% $SpiO_2$, 37° C., 5% $CO_2$) conditions for 30 min. SCOTfluor-84 was added imminently to study uptake under different conditions, followed by washing with 20 mM Hepes, 140 mM NaCl and 0.1% BSA buffer. For the competition assays, the cells were pre-incubated for 1 h at 37° C., 5% $CO_2$ with 5 mM lactic acid. Flow cytometry data were analyzed using FlowJo software.

Zebrafish In Vivo Imaging

Anti-sense glut2 morpholino (5'-ATGACCTGCAGAC AACAAGGACACC-3')[1] was reconstituted to 1 mM in nuclease-free $H_2O$ and injected at 4.2 ng/embryo into the one-cell stage. Embryos were maintained at 28.5° C., according to standard protocols. Wild-type controls and glut2 morphants were injected into the yolk sac at 28 hours post fertilization (hpf) with compound SCOTfluor-89 (50 pmol) and 1 mg mL$^{-1}$ 10,000 MW Dextran Cascade Blue® (ThermoFisher), then embedded in 1% low-melting point agarose for live imaging. Live imaging was performed 30 min post-injection on an inverted Leica SP8 confocal microscope using a HC PL APO CS2 10×/0.40 dry lens. Dextran was excited at 405 nm laser and detected at 415-480 nm, while compound SCOTfluor-89 was excited at 488 nm and detected at 498-600 nm.

TIRF Microscopy

Imaging was performed using a home-built, bespoke single-molecule total internal reflection fluorescence (TIRF) microscope. Fluorophores were excited at 515 nm (SCOTfluor-84). Collimated laser light at 515 nm (Cobolt Fandango-300 DPSS Laser System, Cobalt, Sweden) was aligned and directed parallel to the optical axis at the edge of a 1.49 NA TIRF Objective (CFI Apochromat TIRF 60×C Oil), mounted on an inverted Nikon T12 microscope (Nikon, Japan). The microscope was fitted with a perfect focus system which auto-corrects the z-stage drift during imaging. Fluorescence collected by the same objective was separated from the returning TIR beam by a dichroic mirror DI02-R514 (Semrock) for 515 nm and was passed through appropriate filters [515 nm: BLP01-561R, FF01-607/36 (Semrock)]. Fluorescence was then passed through a 2.5× beam expander and recorded on an EMCCD camera (Delta Evolve 512, Photometrics) operating in frame transfer mode (EM-Gain=11.5 e$^-$/ADU and 250 ADU/photon). Each pixel was 103 nm in length. For single-particle tracking, the images were recorded for 2,000 frames as 20 frames s$^{-1}$. The microscope was automated using the open source microscopy platform Micromanager.[2]

Data Analysis

Single-particle tracking was performed using Trackpy for Python. Particles with a feature size of 15 pixels and a total brightness of 8,000 ADUs for each frame were selected. The detected particles were linked into tracks using a maximum displacement threshold of 10 pixels and a memory of 5 frames. Only those tracks that lasted for more than 5 frames were used in further analysis. For each of the tracks, the mean squared displacement was calculated. A custom written code in Igor Pro (Wavemetrics) was used to generate trajectories, movies, and for further analysis. For each of the mean squared displacement curves, the first five points were fit to a straight line to determine the instantaneous diffusion coefficient from the gradient. The log of these were then binned into histograms of diffusion coefficients.

Metabolic Profiles of Human Cells

Human cell lines were plated in 384 well-plates as 20,000 cells/well and incubated in Krebs-Ringer bicarbonate buffer (KRB: 129 mM NaCl, 4.7 mM KCl, 1.2 mM $KH_2PO_4$, 5 mM $NaHCO_3$, 10 mM HEPES, 2.5 mM $CaCl_2$, 1.2 mM $MgCl_2$ and 0.2% BSA, pH 7.4) at 37° C. for 3 h, after which cells were incubated with SCOTfluor-89 (100 µM), SCOTfluor-84 (25 µM), SCOTfluor-90 (100 µM) for 1 h at 37° C. Cells were washed and resuspended in KRB buffer. Fluorescence intensity measurements were taken on a Biotek Synergy H1 Hybrid Reader [SCOTfluor-89 ($\lambda_{exc.}$: 560 nm; $\lambda_{em.}$: 650 nm), SCOTfluor-84 ($\lambda_{exc.}$: 520 nm; $\lambda_{em.}$: 610 nm), SCOTfluor-90 ($\lambda_{exc.}$: 430 nm; $\lambda_{em.}$: 550 nm)] and their emission values per cell were normalized against the fluorescence intensity of the corresponding solutions in KRB buffer.

The optical properties of SCOTfluor-80, 79, 78, 76 and 81 were compared with the properties of the original NBD. With the exception of triazoles (SCOTfluor-79), all compounds showed longer emission wavelengths than NBD, long Stokes shifts (around 80-100 nm) as shown in Table 1, solvatochromic properties (FIG. 1), good photostability (FIG. 2) and good chemical stability to physiological and oxidative conditions (FIG. 3).

TABLE 1

|     | $\lambda_{abs.}{}^a$ | $\lambda_{em.}{}^a$ | $\varepsilon$ $(M^{-1}cm^{-1})^a$ | $\Phi^b$ |
| --- | --- | --- | --- | --- |
| 80  | 564 | 650 | 27,300 | 0.09 |
| 79  | 420 | 460 | 37,300 | <0.01 |
| 78  | 476 | 548 | 14,600 | 0.54 |
| 76  | 510 | 606 | 16,300 | 0.20 |
| 81  | 546 | 650 | 28,300 | 0.11 |
| NBD | 486 | 542 | 15,400 | 0.55 |

Among SCOTfluors, Se- and C-bridged derivatives displayed emission maxima in the red and NIR emission respectively, and long Stokes shifts (around 100 nm) favouring high signal to background ratios for live-cell imaging. Further-more, SCOTfluors proved compatible for experiments in live cells, showing no significant cytotoxicity in HeLa cells as Shown in FIG. 4. HeLa cells were incubated with SCOTfluor-80, 79, 78, 76, 81, 101, 89, 84 and 90 at 100 µM (1% DMSO, grey bar) and 75 µM (1% DMSO, black bar) for 4 h at 37° C. Cell viabilities were normalized to incubation in cell culture media under the same experimental conditions. A solution of 40% DMSO in cell culture media was used as a known cytotoxic positive control. Values represented as means±s.e.m. (n=3).

Figure 5:
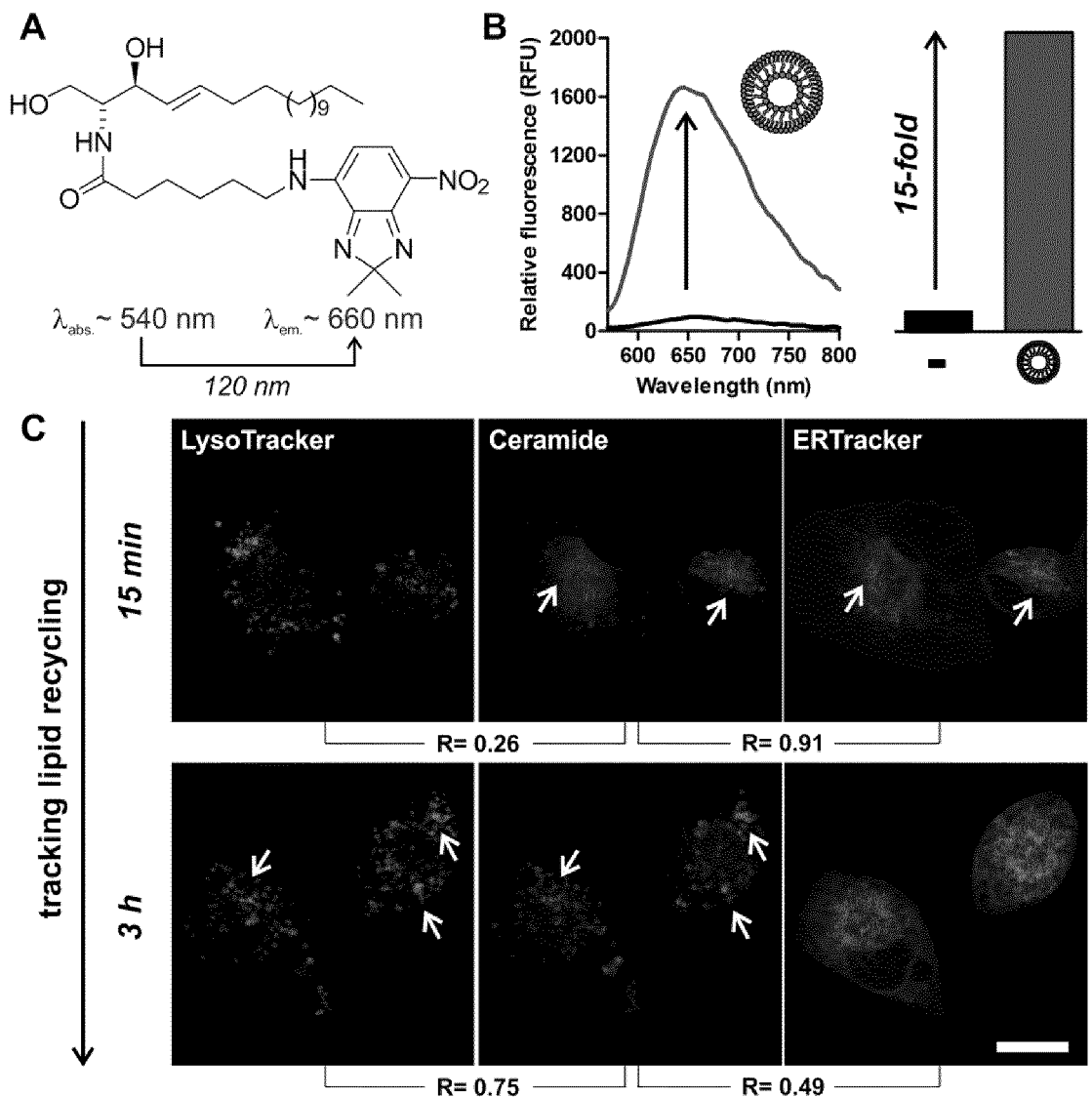

Then, the properties of SCOTfluors for imaging the trafficking of essential metabolites under physiological conditions. Sphingolipids are critical components of membranes in the regulation of cellular metabolism were examined. The dysregulation of sphingolipid metabolism is associated with several diseases and its intracellular localization is crucial to understand metabolic disruption. The C-bridged nitrobenzodiazole core was used to generate the NIR ceramide SCOTfluor-101 (emission>660 nm) and monitor its intracellular localization over time by co-staining with endoplasmic reticulum (ER) and lysosomes markers. Spectral analysis confirmed that the optical properties of SCOTfluor-101 were independent of the sphingoid base and therefore applicable to multiple biolipids. SCOTfluor-101 showed minimal aggregation in water and the incubation with liposomes highlighted its fluorogenic behaviour, with over 15-fold increase in emission as shown in FIG. 5. This property was exploited to visualize the recycling of ceramide SCOTfluor-101 in real time in human A549 cells using fluorescence confocal microscopy. At short times (i.e. 15 min), the ceramide SCOTfluor-101 was mainly found at the Golgi apparatus around the ER, as shown by high co-localization with ER Tracker Green (R=91%) but not LysoTracker Blue (R=26%). Time-lapse imaging demonstrated that the ceramide 8 translocated to the recycling lysosomes after 3 h as highlighted by the increased co-staining with LysoTracker Blue (R=75%).

It was also examined whether SCOTfluors could be used to image in vivo tissues with high metabolic activity. Fluorescent deoxyglucose tracers can monitor glucose uptake in metabo-lically-active cells and tissues, although few have been reported for in vivo use. Herein synthesized compound SCOTfluor-89 was synthetized as an in vivo-compatible glucose analog by nucleophilic substitution of nitrobenzoselenadiazole with 2-deoxyglucosamine. Compound SCOTfluor-89 showed emission around 605 nm with a remarkable Stokes shift of 115 nm, enabling multiplexed imaging with blue and green fluorescent proteins (i.e. BFP and GFP, FIG. 6). The transport of SCOTfluor-89 in HeLa cells transfected with EGFP-tagged GLUT4, the main glucose transporter in mammalian cells was examined. Fluorescence microscopy showed the uptake of SCOTfluor-89 in GLUT4-EGFP cells and co-localization with the transporters (FIG. 6A-C). Notably, the uptake of SCOTfluor-89 was blocked by competition with excess glucose (FIG. 6D-F) and was increased by pre-treating HeLa cells with insulin (FIG. 6H). These results confirm that compound SCOTfluor-89 is a functional substrate of GLUT4 and that enables dual tracking of glucose uptake and its transporters under physiological conditions. Finally, compound SCOTfluor-89 was tested in vivo in zebrafish embryos to visualize regions of high glucose uptake. In vivo administration and imaging of SCOTfluor-89 in wildtype zebrafish embryos indicated bright red fluorescence staining in regions of the developing brain (e.g. midbrain, hindbrain, FIG. 6), which express GLUT2 transporters to supply glucose from circulation. We confirmed that the staining was dependent on the active transport of SCOTfluor-89 through GLUT2 by examining glut2 morpholino-injected zebrafish, which have reduced levels of GLUT2. In vivo images of SCOTfluor-89-treated glut2 morpholino-injected zebrafish showed much weaker fluorescence in the same regions (FIG. 6). SCOTfluor-54 was also tested as a control and observed no tissue-specific staining in wildtype or in glut2 morpholino-injected zebrafish (FIG. 6), highlighting the role of deoxyglucose to recognize GLUT2 transporters. Altogether, these results indicate that SCOTfluor-89 can be used to image glucose uptake in vivo and to perform non-invasive studies of glucose transport in whole intact organisms.

Next, SCOTfluors were used to prepare the first red-fluorescent analogue of lactic acid, an essential metabolite in muscle, blood and cancer cells. Lactic acid is known as a carbon source in cancer cells and its uptake in tumours has been recently linked to aggressive oncological behaviour yet little is known about its traffic and diffusion inside cancer cells. Nitrobenzoselenadiazole was modified with L-isoserine to produce SCOTfluor-84 (FIG. 7, $\lambda_{em.}$~605 nm) as a probe to study the mobilization of lactic acid in live cells. Increased uptake in hypoxic (1% $O_2$) vs normoxic (20% $O_2$) cells was confirmed, since lactic acid can accumulate in environments with low concentrations of oxygen.

Flow cytometry analysis was performed to observe that hypoxic cells were significantly brighter than normoxic cells after incubation with the same concentration of SCOTfluor-84. Competition assays was also performed between SCOTfluor-84 and excess of lactic acid in normoxic cells, which markedly reduced the fluorescence staining, suggesting a common transporter for SCOTfluor-84 and lactic acid in live cells (FIG. 7). Encouraged by these results, the total internal reflection fluorescence (TIRF) microscopy was used to image the real-time diffusion of lactic acid in normoxic and hypoxic cancer cells with super-resolution. For these studies, HeLa cells that had been treated or not with dimethyl-oxalylglycine (DMOG), a permeable prolyl 4-hydroxylase inhibitor that upregulates hypoxia-inducible factors were used.

The paths of over 1,000 individual particles in both untreated (i.e. normoxic) and DMOG-treated (i.e. hypoxic) cells after incubation with SCOTfluor-84 and measured their respective intracellular diffusion coefficients was tracked (FIG. 7, 8). Remarkably, particles in hypoxic cells showed higher mean diffusion coefficients than in normoxic cells, as well as a reduction of the slow diffusion species (FIG. 7, 8). Altogether, these results suggest that hypoxic tumors might display faster recycling rates for intracellular lactic acid than normoxic tumors and prove the utility of SCOTfluor-84 as a new probe for imaging lactic acid metabolism in live cells with high spatiotemporal resolution.

Finally, given the multi-color capabilities of SCOTfluors, they were employed to analyze the metabolic profiles of human cells from different origin. In this study, several human cancer cell lines were incubated with SCOTfluor-101, 84 and 90 as respective analogues of ceramide, lactic acid and glucose. First, the cells were plated at similar densities and incubated them with the probes under the same conditions. Next, their fluorescence emission in the NIR, red and green regions was measured to determine their respective intracellular levels of ceramide, lactic acid and glucose. Notably, different cancer cells presented variability in their metabolite uptake, as represented by their intracellular glucose-lactate and ceramide-lactate ratios. These results demonstrate that SCOTfluors can be combined to generate multiplexed metabolic readouts from live cells, which is not possible in other imaging modalities (FIG. 9).

In conclusion, the present SCOTfluors as small-sized fluorophores covering the entire visible spectrum. SCOTfluors are readily obtained by bridging aminoanilines with different groups and include the smallest NIR-emitting fluorophores to date. SCOTfluors were validated for real-time and in situ imaging of different small biomolecules (e.g. lipids, sugars) in live cells and in vivo, as well as their combination to generate multi-color fingerprints in cells. The tunability and versatility of SCOTfluors will enable non-invasive bioimaging studies of essential metabolites that cannot be performed with conventional fluorophores

The invention claimed is:

1. A compound of formula (I) or a salt thereof

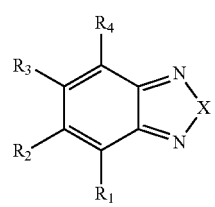

(I)

wherein

X is NH or CR7R8;

R1 is selected from the group consisting of amines, alcohols, thiols, thiophenols, selenols, selenophenols and aryl groups;

R2 and R3 are independently H or a halogen;

R4 is nitro; and

R7 and R8 are independently selected from the group consisting of linear or cyclic alkyl groups containing halogen, amino, cyano or carboxylic ester substituents, and alkyl aryl groups.

2. The compound or a salt thereof according to claim 1 wherein X is CR7R8.

3. The compound or a salt thereof according to claim 1 wherein R1 is an amine.

4. The compound or a salt thereof according to claim 1 wherein R2 and/or R3 are/is H.

5. The compound or a salt thereof according to claim 1 wherein R7 and R8 are independently selected from the group consisting of linear alkyl, cyclic alkyl and aryl groups.

6. The compound according to claim 1, which is selected from the group consisting of:

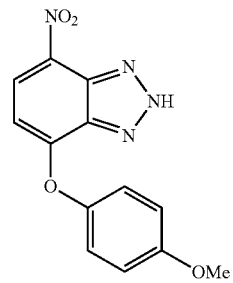

SCOTfluor-29

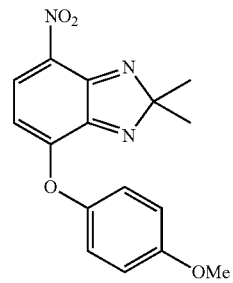

SCOTfluor-30

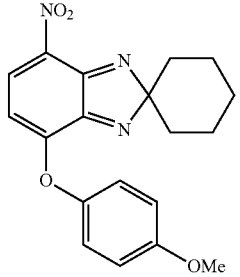

SCOTfluor-31

SCOTfluor-34
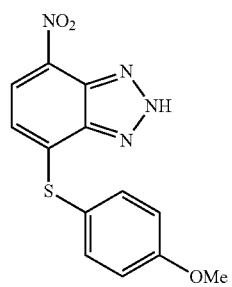
SCOTfluor-35
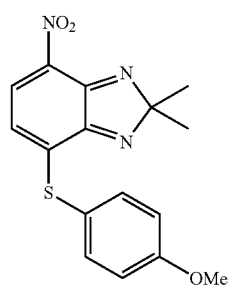
SCOTfluor-36
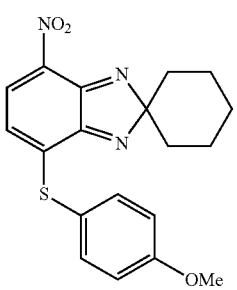
SCOTfluor-39
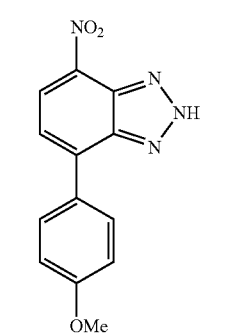
SCOTfluor-40
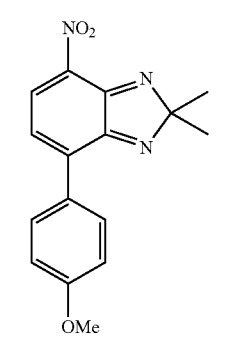
SCOTfluor-41
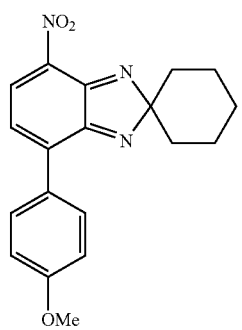
SCOTfluor-44
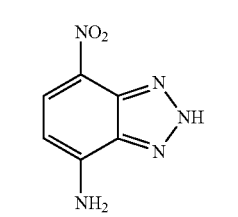
SCOTfluor-45
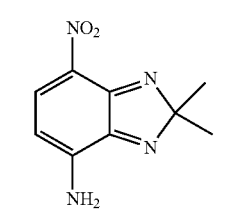
SCOTfluor-46
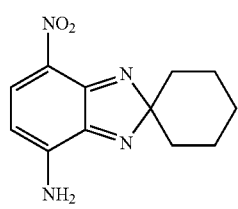
SCOTfluor-49
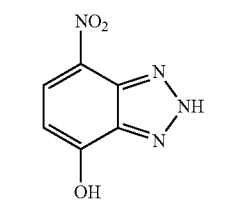
SCOTfluor-50
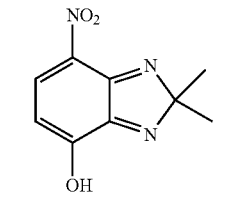
SCOTfluor-51
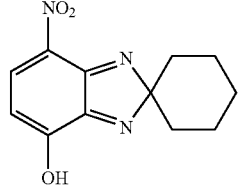

-continued
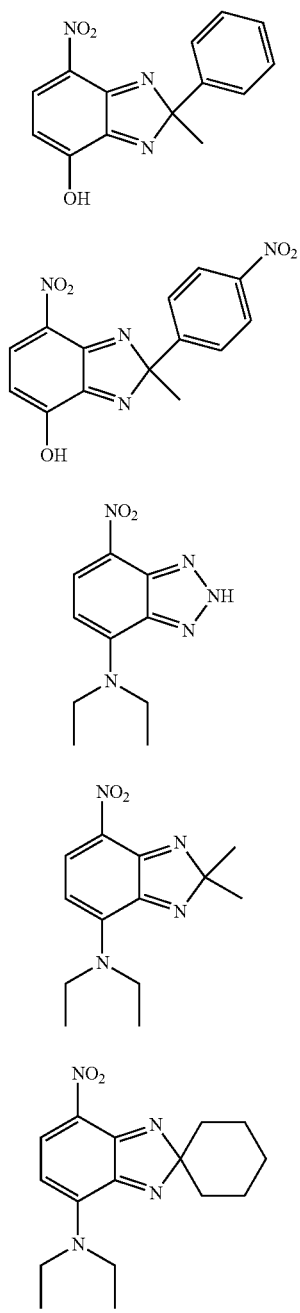
SCOTfluor-52
SCOTfluor-53
SCOTfluor-57
SCOTfluor-58
SCOTfluor-59
SCOTfluor-60
-continued
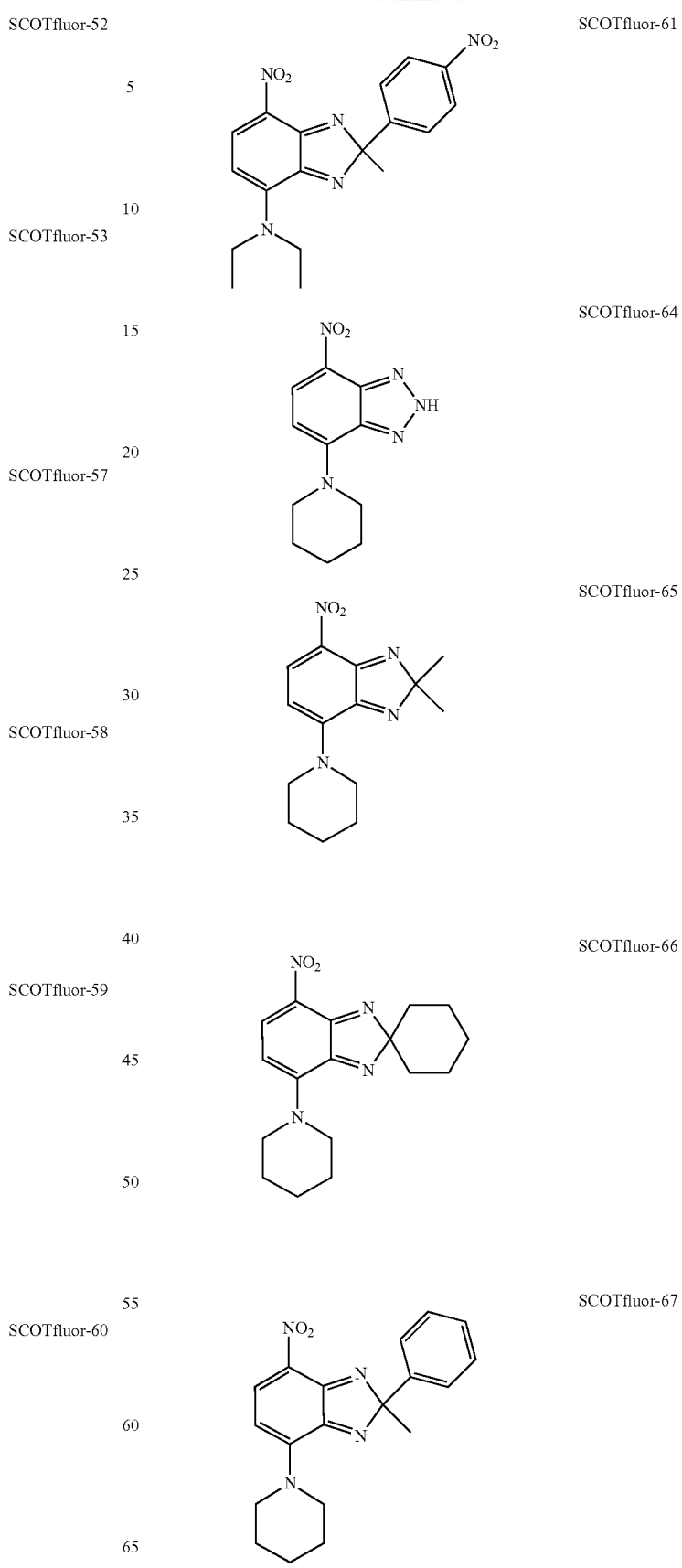
SCOTfluor-61
SCOTfluor-64
SCOTfluor-65
SCOTfluor-66
SCOTfluor-67

-continued
SCOTfluor-68
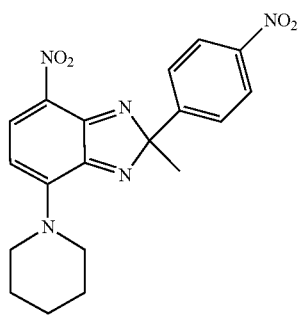
SCOTfluor-71
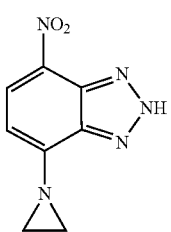
SCOTfluor-72
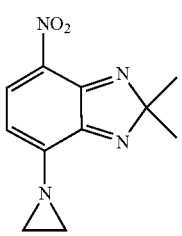
SCOTfluor-73
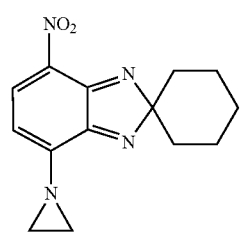
SCOTfluor-74
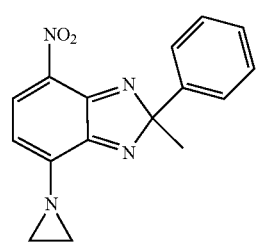
SCOTfluor-75
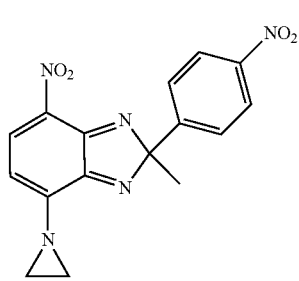
-continued
SCOTfluor-79
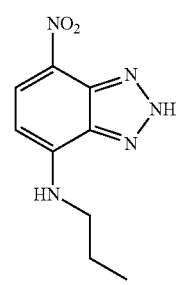
SCOTfluor-80
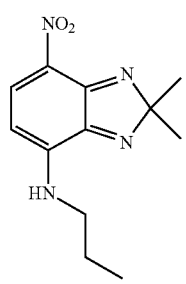
SCOTfluor-81
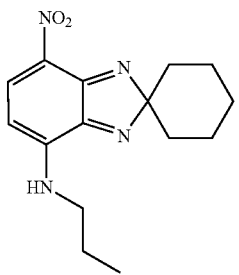
SCOTfluor-82
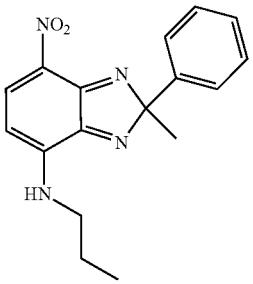
SCOTfluor-83
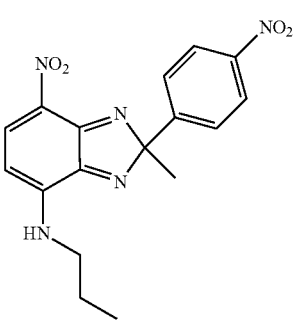

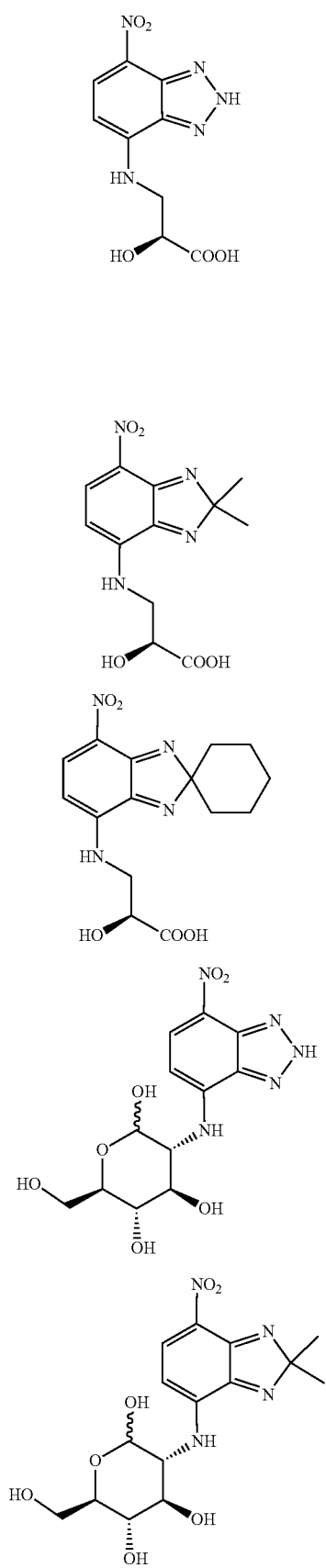

SCOTfluor-101
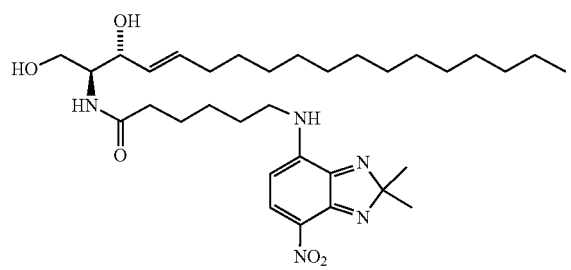
SCOTfluor-140
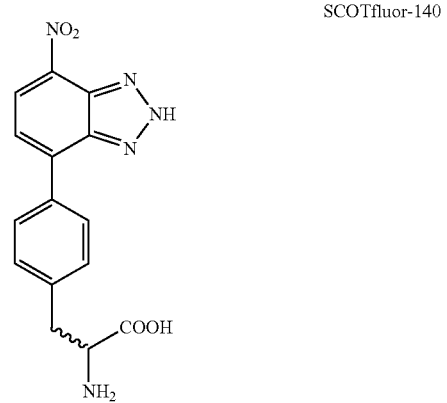
SCOTfluor-141
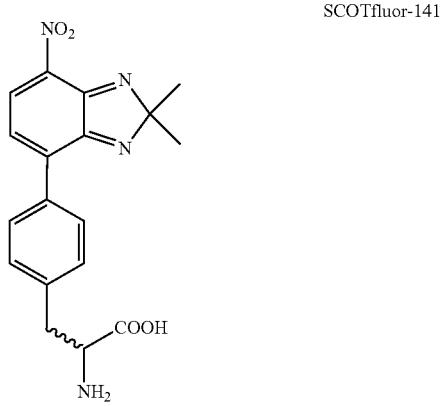
SCOTfluor-142
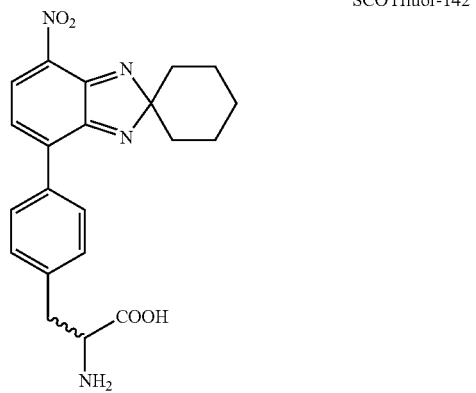
SCOTfluor-152
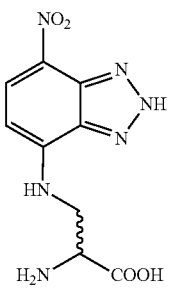
SCOTfluor-153
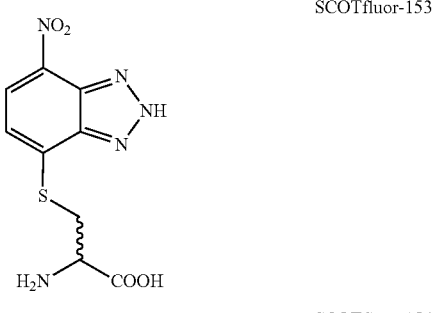
SCOTfluor-154
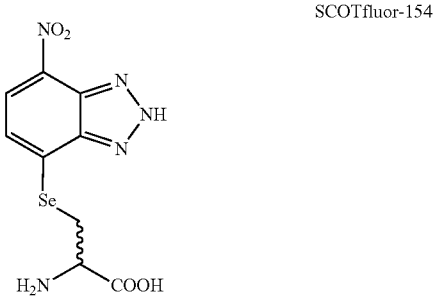
SCOTfluor-155
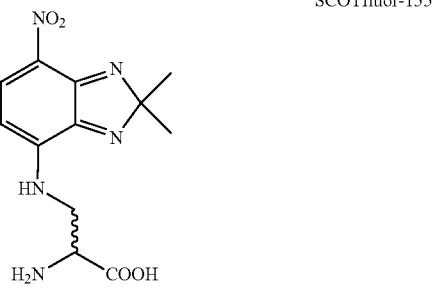
SCOTfluor-156
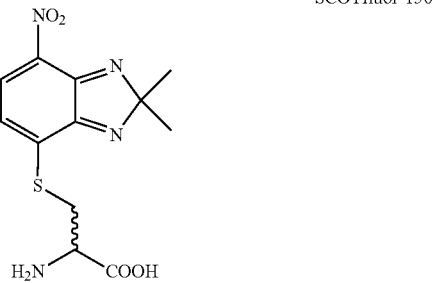

-continued

SCOTfluor-157

[Structure: 4-nitro-2,2-dimethyl-2H-benzimidazole with Se-CH2-CH(NH2)-COOH at position 7]

SCOTfluor-158

[Structure: 4-nitro-spirocyclohexyl-2H-benzimidazole with HN-CH2-CH(NH2)-COOH at position 7]

SCOTfluor-159

[Structure: 4-nitro-spirocyclohexyl-2H-benzimidazole with S-CH2-CH(NH2)-COOH at position 7] and SCOTfluor-160

[Structure: 4-nitro-spirocyclohexyl-2H-benzimidazole with Se-CH2-CH(NH2)-COOH at position 7]

or a salt thereof.

7. The compound according to claim 6, which is selected from the group consisting of:

SCOTfluor-79

[Structure: 4-nitro-7-(propylamino)-2H-benzotriazole]

SCOTfluor-80

[Structure: 4-nitro-2,2-dimethyl-7-(propylamino)-2H-benzimidazole]

SCOTfluor-81

[Structure: 4-nitro-spirocyclohexyl-7-(propylamino)-2H-benzimidazole], and

SCOTfluor-101

[Structure: ceramide linked via amide to hexyl-NH to 2,2-dimethyl-4,7-dinitro-benzimidazole]

or a salt thereof.

8. A process for the preparation of the compound derivative or a salt thereof according to claim 1, said process comprising the step of:

a) providing an intermediate of formula II $$\text{(II)}$$

[Structure: benzene ring with R4, NH2, NH2, R, R2, R3 substituents]

wherein
R is a halogen atom;
R2 and R3 are independently H or a halogen; and
R4 is either H, nitro or cyano;

b) linking the two amino groups; and c) performing a substitution reaction to replace the halogen with a nucleophile group.

9. A precursor compound of Formula (1a) or salt thereof

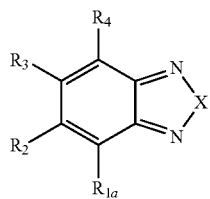
(1a)

wherein X, $R_2$, $R_3$, $R_4$ are as defined as in claim 1 and $R_{1a}$ is halogen.

10. A method of therapy, diagnosis, surgery, or analysis, the method comprising use of a compound or a salt thereof according to claim 1.

11. The method according to claim 10 wherein the method is selected from the group consisting of optical coherence tomography, fluorescence spectroscopy, fluorimetry, fluorescence lifetime, fluorescence microscopy, fluorescence tomography, whole-body fluorescence imaging, flow cytometry, fluorescence-assisted cell sorting, fluorescence-guided surgery, fluorescence endomicroscopy, multi-spectral optoacoustic imaging, Raman spectroscopy, Raman imaging, fundus camera imaging and angiography.

12. The method according to claim 10 wherein the method comprises labelling, tracking, and/or imaging cells, tissues and organs in vivo, in vitro or ex vivo.

13. The method according to claim 10, wherein the method is fluorescence-guided surgery of cancer or fluorescent probes for diagnosis of protein aggregates in neurodegenerative diseases.

* * * * *